US010350261B2

(12) United States Patent
Esmon et al.

(10) Patent No.: US 10,350,261 B2
(45) Date of Patent: *Jul. 16, 2019

(54) EXTRACELLULAR HISTONES AS BIOMARKERS FOR PROGNOSIS AND MOLECULAR TARGETS FOR THERAPY

(71) Applicant: OKLAHOMA MEDICAL RESEARCH FOUNDATION, Oklahoma City, OK (US)

(72) Inventors: Charles T. Esmon, Oklahoma City, OK (US); Jun Xu, Edmond, OK (US); Xiaomei Zhang, Edmond, OK (US)

(73) Assignee: OKLAHOMA MEDICAL RESEARCH FOUNDATION, Oklahoma City, OK (US)

( * ) Notice: Subject to any disclaimer, the term of this patent is extended or adjusted under 35 U.S.C. 154(b) by 491 days.

This patent is subject to a terminal disclaimer.

(21) Appl. No.: 14/734,238

(22) Filed: Jun. 9, 2015

(65) Prior Publication Data

US 2015/0344556 A1 Dec. 3, 2015

Related U.S. Application Data

(60) Continuation of application No. 14/270,470, filed on May 6, 2014, which is a division of application No. 12/266,336, filed on Nov. 6, 2008, now Pat. No. 8,716,218.

(60) Provisional application No. 60/985,886, filed on Nov. 6, 2007.

(51) Int. Cl.
| | |
|---|---|
| *A61K 39/395* | (2006.01) |
| *A61K 38/10* | (2006.01) |
| *A61K 31/727* | (2006.01) |
| *A61K 38/17* | (2006.01) |
| *A61K 38/48* | (2006.01) |
| *A61K 45/06* | (2006.01) |
| *C07K 16/18* | (2006.01) |
| *C07K 16/40* | (2006.01) |
| *G01N 33/68* | (2006.01) |
| *A61K 38/36* | (2006.01) |
| *C07K 7/08* | (2006.01) |
| *A61K 39/00* | (2006.01) |

(52) U.S. Cl.
CPC ............ *A61K 38/10* (2013.01); *A61K 31/727* (2013.01); *A61K 38/1709* (2013.01); *A61K 38/36* (2013.01); *A61K 38/4833* (2013.01); *A61K 38/4846* (2013.01); *A61K 38/4866* (2013.01); *A61K 39/3955* (2013.01); *A61K 45/06* (2013.01); *C07K 7/08* (2013.01); *C07K 16/18* (2013.01); *C07K 16/40* (2013.01); *C12Y 304/21005* (2013.01); *C12Y 304/21006* (2013.01); *G01N 33/6875* (2013.01); *A61K 2039/505* (2013.01); *C07K 2317/76* (2013.01); *C12Y 304/21069* (2013.01)

(58) Field of Classification Search
None
See application file for complete search history.

(56) References Cited

U.S. PATENT DOCUMENTS

| | | | | |
|---|---|---|---|---|
| 7,728,114 | B2 * | 6/2010 | Mach .............. | C07K 16/2809 530/388.15 |
| 8,716,218 | B2 | 5/2014 | Esmon et al. | |
| 2003/0021797 | A1 | 1/2003 | Datta et al. | |
| 2005/0118277 | A1 | 6/2005 | Wormser | |
| 2007/0093426 | A1 | 4/2007 | Wormser | |

FOREIGN PATENT DOCUMENTS

| | | |
|---|---|---|
| EP | 1544214 | 6/2005 |
| JP | 2005-041810 | 2/2005 |
| JP | 2007-246473 | 9/2007 |
| JP | 2010-532342 | 10/2010 |

OTHER PUBLICATIONS

Berger et al., World J Gastroenterol Oct. 14, 2007; 13(38): 5043-5051. (Year: 2007).*
Pietruczuk et al., World J Gastroenterol Sep. 7, 2006 ; 12(33): 5344-5351. (Year:2006).*
Lindstrom et al., Critical Care 2006, 10:R16, pp. 1-9. (Year: 2006).*
Alsfasser et al., Arch Surg. Jul. 2006; 141(7): 670-677. (Year: 2006).*
Toltl et al., Front Biosci. Jan. 1, 2007;12:1963-72 (Year: 2007).*
Robert W. Bahr, Deputy Commissioner for Patent Examination Policy memorandum of Feb. 22, 2018, 2 pages. (Year: 2018).*
Harlow et al. (Antibodies, A Laboratory Manual, Cold Spring Harbor laboratory, 1988, pp. 37-47. (Year: 1988).*
Edwards et al. (J. Mol. Biol. (2003) 334, 103-118). (Year: 2003).*
Meyer et al. (British Journal of Haematology, 2018, 180, 808-820. (Year: 2018).*
Lloyd et al., Protein Engineering, Design & Selection vol. 22 No. 3 pp. 159-168, 2009. (Year: 2009).*
Abakushin et al., "Histones evoke thymocyte death in vitro; histone-binding immunoglobulins decrease their cytotoxicity," *Biochemistry (Mosc)*, 64 (6): 693-698, 1999.
Ambrosio et al., "The heparin-binding lectin from ovine placenta: purification and identification as histone H4," *Glycoconjugate Journal.*, 14:831-836, 1997.
Brinkmann et al., "Neutrophil extracellular traps kill bacteria," *Science*, 303 (5663): 1532-1535, 2004.
Clark et al., "Platelet TLR4 activates neutrophil extracellular traps to ensnare bacteria in septic blood," *Nat. Med.*, 13 (4): 463-469, 2007.

(Continued)

*Primary Examiner* — Zachary S Skelding
(74) *Attorney, Agent, or Firm* — Parker Highlander PLLC

(57) ABSTRACT

Hyper-inflammatory responses can lead to a variety of diseases including sepsis. It is now shown that extracellular histones released in response to inflammatory challenge are mediators contributing to endothelial dysfunction, organ failure and death during sepsis. As such, they can be targeted pharmacologically by inhibitors, as well as used as biomarkers for prognosis of sepsis and other diseases.

23 Claims, 27 Drawing Sheets

Specification includes a Sequence Listing.

(56) References Cited

OTHER PUBLICATIONS

Currie et al., "Reduction of histone cytotoxicity by the Alzheimer beta-amyloid peptide precursor," *Biochem. Biophys. Acta*, 1355 (3): 248-258, 1997.
Emlen et al., "Regulation of nuclear antigen expression on the cell surface of human monocytes," *J. Immunol.*, 148 (10): 3042-3048, 1992.
Esmon et al., "Antiphospholipid antibodies and the protein C pathway," *J. Autoimmun.*, 15 (2): 221-225, 2000.
Gaini et al., "High mobility group box-1 protein in patients with suspected community-acquired infections and sepsis: a prospective study," *Crit. Care*, 11 (2): R32, 2007.
Genbank Protein, Accession No. CAA4764.1, Histone [*Homo sapiens*], Apr. 18, 2005.
Gonias et al., "Precipitation of fibrinogen, fibrinogen degradation products and fibrin monomer by histone H3," *Thromb. Res.*, 39(1):97-116, 1985.
Gupta et al., "Role of protein C in renal dysfunction after polymicrobial sepsis," *J. Am. Soc. Nephrol.*, 18 (3): 860-867, 2007.
Herren et al., "Identification of histone H2B as a regulated plasminogen receptor," *Biochemistry*, 45 (31): 9463-9474, 2006.
Hirsch, "Bactericidal action of histone," *J. Exp. Med.*, 108 (6): 925-944, 1958.
Kalaaji et al., "Glomerular apoptotic nucleosomes are central target structures for nephritogenic antibodies in human SLE nephritis," *Kidney Int.*, 71 (7): 664-672, 2007.
Kleine et al., "Histone-induced damage of a mammalian epithelium: the role of protein and membrane structure," *Am. J. Physiol.*, 273 (6 Part 1): C1925-C1936, 1997.
Lay et al., "Acute inflammation is exacerbated in mice genetically predisposed to a severe protein C deficiency," *Blood*, 109 (5): 1984-1991, 2007.
Ma and Kubes, "Platelets, neutrophils, and neutrophil extracellular traps (NETs) in sepsis," *J. Thromb. Haemost.*, 6 (3): 415-420, 2008.
Macias and Nelson, "Severe protein C deficiency predicts early death in severe sepsis," *Crit. Care Med.*, 32 (5 Supp.): S223-S228, 2004.
Office Communication issued in Australian Patent Application No. 2008323947 dated Feb. 28, 2013.
Office Communication issued in Canadian Patent Application No. 2,704,974, dated Jan. 7, 2015.
Office Communication issued in European Patent Application No. 08847874.8 dated Nov. 12, 2012.
Office Communication issued in European Patent Application No. 08847874.8 dated Nov. 17, 2010.
Office Communication issued in European Patent Application No. 08847874.8 dated Jun. 12, 2014.
Office Communication issued in European Patent Application No. 08847874.8 dated May 8, 2015.
Office Communication issued in Japanese Patent Application No. 2010-532342, dated Jan. 22, 2014.
Office Communication issued in Japanese Patent Application No. 2010-532342, dated Jul. 8, 2013.
Office Communication issued in U.S. Appl. No. 12/266,336 dated Oct. 5, 2010.
Office Communication issued in U.S. Appl. No. 12/266,336 dated May 23, 2011.
Office Communication issued in U.S. Appl. No. 12/266,336 dated Aug. 22, 2011.
Office Communication issued in U.S. Appl. No. 12/266,336 dated Sep. 12, 2011.
Office Communication issued in U.S. Appl. No. 12/266,336 dated Aug. 26, 2013.
Office Communication issued in U.S. Appl. No. 12/266,336 dated Aug. 5, 2011.
Office Communication issued in U.S. Appl. No. 12/266,336 dated Jun. 14, 2010.
Parsenghian et al., "Beyond the walls of the nucleus: the role of histones in cellular signaling and innate immunity," *Biochem. Cell. Biol.*, 84(4):589-604, 2006.
PCT International Search Report and Written Opinion issued in Application No. PCT/US2008/082632 dated Feb. 16, 2009.
Radic et al., "Nucleosomes are exposed at the cell surface in apoptosis," *J. Immunol.* 172 (11): 6692-6700, 2004.
Response (Supplemental) to Office Communication issued in Australian Patent Application No. 2008323947 dated Jan. 20, 2014.
Response (untranslated) to Office Communication issued in Japanese Patent Application No. 2010-532342, dated Dec. 20, 2013.
Response to Office Communication issued in Australian Patent Application No. 2008323947 dated Dec. 23, 2013.
Response to Office Communication issued in European Patent Application No. 08847874.8 dated Mar. 15, 2011.
Response to Office Communication issued in European Patent Application No. 08847874.8 dated Mar. 22, 2013.
Response to Office Communication issued in Japanese Patent Application No. 2010-532342, dated Dec. 20, 2013.
Response to Office Communication issued in U.S. Appl. No. 12/266,336 dated Feb. 3, 2011.
Response to Office Communication issued in U.S. Appl. No. 12/266,336 dated Jul. 20, 2011.
Response to Office Communication issued in U.S. Appl. No. 12/266,336 dated Aug. 8, 2011.
Response to Office Communication issued in U.S. Appl. No. 12/266,336 dated Aug. 25, 2011.
Response to Office Communication issued in U.S. Appl. No. 12/266,336 dated Nov. 26, 2013.
Rouhiainen et al., "Pivotal advance: analysis of proinflammatory activity of highly purified eukaryotic recombinant HMGB1 (amphoterin)," *J. Leukoc. Biol.*, 81 (1): 49-58, 2007.
Vani et al., "Histone H1 inhibits the proliferation of MCF 7 and MDA MB 231 human breast cancer cells," *Cell Biology International*, 30:326 - 331, 2006.
Xiao et al., "Protein-bound heparin/heparan sulfates in human adult and umbilical cord plasma," *Haemostasis*, 29(4):237-246, 1999.
Xu et al., "Extracellular histones are major mediators of death in sepsis," *Nat. Med.*, 15(11):1318-1321, 2009.
Zorio et al., "Circulating activated protein C is reduced in young survivors of myocardial infarction and inversely correlates with the severity of coronary lesions," *Journal of Thrombosis and Haemostasis*, 4:1530-1536, 2006.
Office Communication issued in Canadian Patent Application No. 2,704,974, dated May 5, 2017.
Batova et al., "Human recombinant Fab fragments with sub-nanomolar affinities for acetylated histones,"*Journal of Immunological Methods*, 329(1-2):1-10, 2008.
Ilmakunnas et al., "Activation of protein C during reperfusion in clinical liver transplantation," *Transplantation*, 75(4):467-472, 2003.
MacLaren et al., "Emerging role of anticoagulants and fibrinolytics in the treatment of acute respiratory distress syndrome" *Pharmacotherapy*, 27(6):860-873, 2007.
Monestier et al., "Structure and binding properties of monoclonal antibodies to core histones from autoimmune mice," *Molecular Immunology*, 30(12):1069-1075, 1993.
Office Communication issued in U.S. Appl. No. 14/270,470, dated Jan. 30, 2018.
Office Communication issued in U.S. Appl. No. 14/270,470, dated Jul. 9, 2018.
Office Communication issued in U.S. Appl. No. 14/270,470, dated Nov. 7, 2018.
Office Communication issued in U.S. Appl. No. 14/270,470, dated Oct. 19, 2017.
Office Communication issued in U.S. Appl. No. 14/270,470, dated May 10, 2017.
Office Communication issued in U.S. Appl. No. 14/270,470, dated Dec. 9, 2016.
Portanova et al., "Anti-histone antibodies in idiopathic and drug-induced lupus recognize distinct intrahistone regions," *J. of Immun.*, 138(2):446-451, 1987.
Tabers Cyclopedic Medical Dictionary, F.A. Davis O., Clayton Thomas, Ed., pp. 986-987, 1993.

(56) References Cited

OTHER PUBLICATIONS

Urban et al., "Neutrophil extracellular traps capture and kill Candida albicans yeast and hyphal forms," *Cell Microbiol.*, 8(4):668-76, 2006.

* cited by examiner

E.coli B7

E.coli B7+Histones

E.coli B7+H4

E.coli B7+H4P39

E.coli M15

E.coli M15+Histones

E.coli M15+H4

E.coli M15+H4P39

EXTRACELLULAR HISTONES AS BIOMARKERS FOR PROGNOSIS AND MOLECULAR TARGETS FOR THERAPY

This application is a continuation of co-pending U.S. patent application Ser. No. 14/270,470, filed May 6, 2014, which is a divisional of U.S. patent application Ser. No. 12/266,336, filed Nov. 6, 2008, now U.S. Pat. No. 8,716, 218, issued May 6, 2014, which claims benefit of U.S. Provisional Application Ser. No. 60/985,886, filed Nov. 6, 2007. The entire text of each of the above-referenced disclosures is specifically incorporated herein by reference without disclaimer.

The sequence listing that is contained in the file named "OMRFP0090USC1_ST25.txt", which is 7 KB (as measured in Microsoft Windows®) and was created on Jun. 5, 2015, is filed herewith by electronic submission and is incorporated by reference herein.

BACKGROUND OF THE INVENTION

I. Field of the Invention

The present invention relates to the fields of medicine, molecular and cell biology. More particularly, it relates to the identification of extracellular histones as mediators of cellular toxicity, and their use as targets in both diagnostic and therapeutic methods.

II. Related Art

Hyper-inflammatory responses to infection contribute to sepsis. The current understanding of pathogenesis of sepsis is that release of pro-inflammatory cytokines by host cells in response to the invading pathogens causes tissue injury and lethality. Tumor necrosis factor (TNF) and interleukin 1β (IL-1β) from macrophages stimulated by lipopolysaccharide (LPS) were identified as early mediators and high mobility group box-1 protein (HMGB1) was identified as a late mediator₁. Although inhibiting these mediators is protective in animal models, clinical trials of TNF and IL-1β as therapeutic targets in sepsis failed (Wang et al., 1999). Although HMGB1 is a potential therapeutic target in septic patients, recent studies indicate that HMGB1 itself is a weak pro-inflammatory cytokine and levels of HMGB1 correlated only weakly to other pro-inflammatory markers in patients with suspected community-acquired infections and sepsis (Rouhiainen et al., 2007; Gaini et al., 2007).

At present, recombinant human activated protein C (APC) is the only pharmacological agent approved for the treatment of severe sepsis patients with organ failure and a high risk of death (Bernard et al., 2001; Baltch et al., 2007). Although anti-coagulation, anti-inflammatory and cytoprotective functions of APC appear to contribute to the protection in animal models, the mechanism by which APC improves the clinical outcome is unknown (Russell, 2006). Protein C is converted to APC by thrombin complexed with thrombomodulin (TM) on the endothelium. APC cleaves activated factor V and factor VIII, thus negatively down-regulating thrombin formation and maintaining the hemostatic balance in vivo (Esmon, 2003). APC protects animal from *E. coli* mediated septic lethality (Taylor et al., 1987). Clinical trials of two other anti-coagulant therapies, anti-thrombin III and tissue factor-pathway inhibitor, failed to improve survival of septic patients, suggesting that modulation of coagulation may not be the primary mechanism underlying the therapeutic benefit from APC treatment in sepsis (Russell, 2006).

SUMMARY OF THE INVENTION

Thus, in accordance with the present invention, there is provided a method of inhibiting a medical condition involving extracellular histone cytotoxicity in a subject comprising administering to a subject a first inhibitor histone cytotoxicity, wherein the first inhibitor is not an H2A peptide, and wherein the condition is not systemic lupus erythematosus (SLE). The first inhibitor may comprise an H1, H2B, H3 or H4 histone fragment or peptide, such as an H4 peptide comprising residues 50-67 of H4 (SEQ ID NO: 19). The method may further comprise administering to the subject a second inhibitor of histone cytotoxicity, such as an H1, H2A, H2B, H3 or H4 histone fragment or peptide that is distinct from the first inhibitor, or a cocktail of at least three distinct histone fragments or peptides, including a cocktail comprising H3 and H4 peptides. The subject may be a human, dog, cat, horse, monkey, mouse, rat, rabbit, sheep, goat, cow or pig.

The method may further comprise administering to the subject an anti-inflammatory agent and/or activated protein C. The first inhibitor of histone cytotoxicity may be an anti-histone antibody, such as one that binds to H1, H2A, H2B, H3 or H4. The first inhibitor of histone cytotoxicity may also be a cocktail of antibodies that binds to three or more of an H1, H2A, H2B, H3 or H4. The first inhibitor of histone cytotoxicity may comprise a cocktail of at least one histone fragment or peptide and at least one anti-histone antibody. The first inhibitor of histone cytotoxicity may be granzyme A or B, plasmin, Factor 7 activating protease or heparin. The disease may be bacterial sepsis, fungal sepsis, surgery, traumatic hemorrhage and/or tissue damage, acute pancreatitis, acute respiratory distress syndrome, ischemia-reperfusion injury, cardiovascular disease, autoimmune disease other than SLE, chemotherapy toxicity, radiotherapy toxicity, cytokine therapy toxicity, or burn.

In another embodiment, there is provided a method of inhibiting a non-septic disease state involving extracellular histone cytotoxicity in a subject comprising administering to a subject a first inhibitor histone cytotoxicity, and wherein the disease state is not systemic lupus erythematosus (SLE).

In still yet another embodiment, there is provided a method of determining a subjects' disease prognosis comprising (a) obtaining a serum or plasma sample from the subject; and (b) determining the extracellular histone content of the sample, wherein the presence of extracellular histone in the sample indicates that the subject is at risk of disease progression. Step (b) may comprise ELISA or Western blotting using anti-histone antibodies. The method may further comprise treating the subject with an anti-inflammatory agent or an inhibitor of extracellular histone cytotoxicity.

In yet additional embodiments, there are provided (a) a pharmaceutical composition comprising peptides from at least three of histone H1, H2A, H2B, H3 and H4, including peptides from each of H1, H2A, H2B, H3 and H4; (b) a pharmaceutical composition comprising antibodies that bind to at least three of histone H1, H2A, H2B, H3 and H4, including antibodies bind to each of H1, H2A, H2B, H3 and H4; and (c) compositions as in (a) and (b) and further comprising activated protein C.

In still a further embodiment, there is provided a method of inhibiting pro-inflammatory cytokine production by endothelial cells in a subject comprising administering to the subject a first inhibitor histone cytotoxicity, wherein the first inhibitor is not an H2A peptide. The subject, in particular embodiments, does not have systemic lupus erythematosus (SLE). The pro-inflammatory cytokine may be IL-6 or IL-8. The first inhibitor may comprise an H1, H2B, H3 or H4 histone fragment or peptide. The H4 peptide may comprise residues 50-67 of H4 (SEQ ID NO: 19). The method may further comprise administering to the subject a second inhibitor of histone cytotoxicity, such as an H1, H2A, H2B, H3 or H4 histone fragment or peptide that is distinct from the first inhibitor. The method may further comprise administering to the subject a cocktail of at least three distinct histone fragments or peptides. The subject may be a human, dog, cat, horse, monkey, mouse, rat, rabbit, sheep, goat, cow or pig. The first inhibitor of histone cytotoxicity may be an anti-histone antibody, such as an anti-histone antibody that binds to H1, H2A, H2B, H3 or H4. The first inhibitor of histone cytotoxicity may be a cocktail of antibodies that binds to three or more of H1, H2A, H2B, H3 or H4. The first inhibitor of histone cytotoxicity may comprise a cocktail of at least one histone fragment or peptide and at least one anti-histone antibody. The subject may suffer from chronic cardiovascular disease, such as athlerosclereosis, or tumor angiogenesis or trauma.

In still yet a further embodiment, there is provided a method of reducing endothelial permeability in a subject comprising administering to the subject a first inhibitor histone cytotoxicity, wherein the first inhibitor is not an H2A peptide. In some embodiments, the subject does not have systemic lupus erythematosus (SLE). In other embodiments, the subject has contacted anthrax or suffers from edema, vascular leak, or shock, including circulatory shock. The first inhibitor may comprise an H1, H2B, H3 or H4 histone fragment or peptide. The H4 peptide may comprise residues 50-67 of H4 (SEQ ID NO: 19). The method may further comprise administering to the subject a second inhibitor of histone cytotoxicity, such as an H1, H2A, H2B, H3 or H4 histone fragment or peptide that is distinct from the first inhibitor. The method may further comprise administering to the subject a cocktail of at least three distinct histone fragments or peptides. The subject may be a human, dog, cat, horse, monkey, mouse, rat, rabbit, sheep, goat, cow or pig. The first inhibitor of histone cytotoxicity may be an anti-histone antibody, such as an anti-histone antibody that binds to H1, H2A, H2B, H3 or H4. The first inhibitor of histone cytotoxicity may be a cocktail of antibodies that binds to three or more of H1, H2A, H2B, H3 or H4. The first inhibitor of histone cytotoxicity may comprise a cocktail of at least one histone fragment or peptide and at least one anti-histone antibody.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) EPCR or TM mRNA expression levels from indicated organs of mice (n=3) were determined by real time PCR and expressed as percentage of the level in spleen for EPCR and lung for TM. (FIG. 1B) EPCR or TM mRNA expression levels from indicated organs of mice (n=4) 18 hr after LPS challenge (10 mg/kg i.v.) were determined by real time PCR and expressed as fold change compared to the levels of expression in mice treated with saline (n=4). (FIG. 1C) Organ tissue extracts were immunoprecipitated by RMEPCR1560, separated by SDSPAGE and immunoblotted by biotin-labeled RMEPCR1543.

(FIG. 2A) EPCR or (FIG. 2B) TM surface expression was measured by flow cytometry with anti-EPCR or anti-TM mAb.

(FIG. 3A) Protein C activation was measured on mouse peritoneal macrophages stimulated with or without LPS (1 µg/ml), IFN (20 ng/ml) or both for 24 hr, with 100 nM mouse protein C and 10 nM bovine thrombin in the absence or presence of 200 nM anti-EPCR mAb for 30 min at 37° C. APC activity was determined by its amidolytic activity toward chromogenic substrates. (FIG. 3B) Thrombin generation was measured with the same condition in (FIG. 3A) except using 200 nM bovine prothrombin, 3 nM bovine factor V and 85 nM bovine factor X instead of 10 nM bovine thrombin, in the absence or presence of 100 nM mouse protein C. (FIG. 3C) APC activity was measured under the condition (FIG. 3B) in the presence of mouse protein C.

(FIG. 4A) Western blot of concentrated conditioned medium of RAW cells or activated RAW cells with LPS and IFN in the absence or presence of APC. (FIG. 4B) Purified histone H4 was incubated with or without APC and subject to SDS-PAGE and staining.

(FIG. 13A) EA.hy926 cells were cultured with calf thymus histones (50 µg/ml) or calf thymus histone H1, H2A, H2B, H3 or H4 (20 µg/ml) for 1 hr at 37° C. Cell damage was measured by flow cytometry for PI staining (FIG. 13B) APC (100 nM) was absent or present during the incubations with histones, histone H3 or H4 in the above assays. (FIG. 13C) Purified calf thymus histone H3 (top panel) or histone H4 (bottom panel) (100 µg/ml) was incubated in Opti-MEM medium with the indicated concentrations of human APC for 1 hr at 37° C. Samples were then subjected to SDS-PAGE and coomassie blue staining (FIG. 13D) Purified calf thymus histone H3 (top panel) or histone H4 (bottom panel) (100 µg/ml) was incubated in Opti-MEM medium with 10 nM human APC in the absence or presence of 0.5 mg/ml PS/PC or PE/PS/PC liposomes for 1 hr at 37° C. Samples were then subjected to SDS-PAGE and coomassie blue staining.

(FIG. 14A) EA.hy926 cells were cultured with calf thymus histones in the indicated concentration in the absence or presence of APC (10 or 100 nM) at 37° C. for 1 hr. Cell damage was measured by flow cytometry for PI staining and expressed as mean fluorescence index (MFI). (FIG. 14B) Calf thymus histones in Opti-MEM medium was incubated with APC (100 nM) at 37° C. for the indicated time and then mixed with PPACK (10 µM) to inactivate APC. The above medium was used to culture EA.hy926 cells for 1 hr for cytotoxicity assay or (FIG. 14C) subjected to SDS-PAGE and Western blotting for histone H3 or H4. (FIG. 14D) EA.hy926 cells were cultured with calf thymus histones (50 µg/ml) in the absence or presence of protein C (100 nM), thrombin (T) (10 nM) or APC (100 nM) at 37° C. for 30 min. Cell damage was measured by flow cytometry for PI staining (FIG. 14E) Indicated time points of baboon plasma samples after *E. coli* or *E. coli* plus APC challenge were subjected to SDS-PAGE and Western blotting for histone H3.

(FIG. 15A) Mice were injected intravenously with a high dose of LPS (10 mg/kg) with anti-histone H4 or mouse IgG control mAb (20 mg/kg). Survival rates of each group are indicated. (FIG. 15B) Mice were injected intravenously with a low dose of LPS (1 mg/kg) with or without anti-PC mAb (2.5 mg/kg), and with anti-histone H4 or histone H2B mAb (20 mg/kg). Survival rates of each group are indicated. (FIG. 15C) Mouse plasma was collected 6 hr after LPS or LPS plus mAb challenge and subjected to Western blotting for histone H3.

DETAILED DESCRIPTION OF THE INVENTION

Figure 1A:
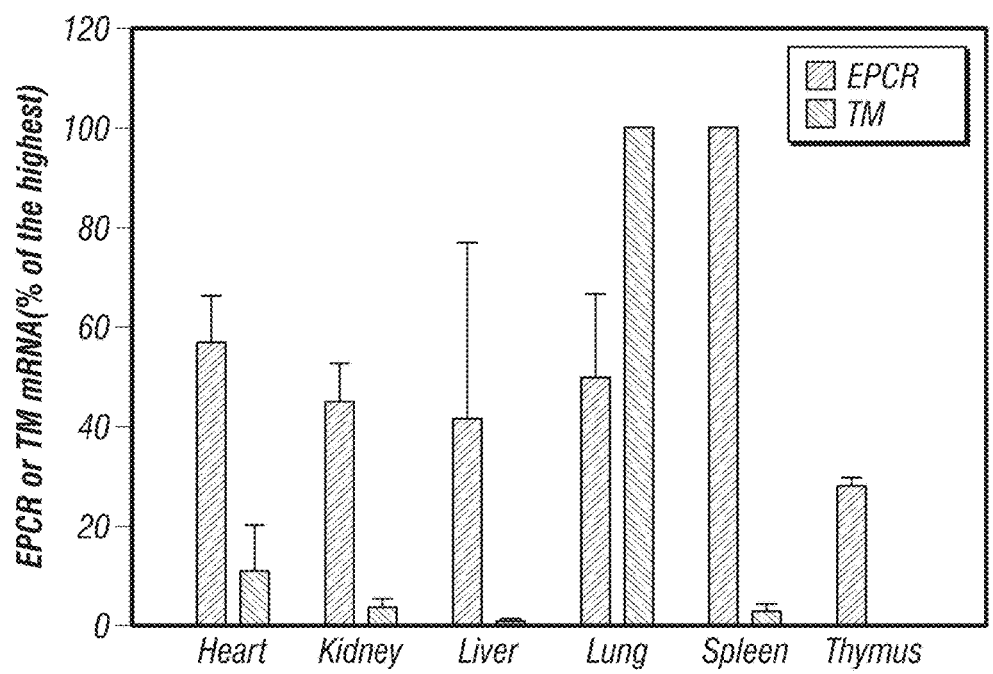
FIGS. 1A-C—Differential expression of EPCR and TM in mouse organs.

Histones have been known as intranuclear DNA binding proteins involved in gene regulation for more than 100 years. Histones also have antibacterial activities and histone H3 and H4 are the major contributors to this function (Hirsch, 1958). The inventors now show that extracellular histones, in particular histones H3 and H4, are cytotoxic toward endothelium and injection of histones causes lethality of mice. Thus, extracellular histones should be considered as potential biomarkers for prognosis and molecular targets for therapeutics in addition to APC for sepsis and other diseases.

A novel mechanism of killing bacteria extracellularly by neutrophil extracellular traps (NETs) was recently observed both in vitro and in vivo (Brinkmann et al., 2004). NETs are composed of granular proteins, DNA and histone H1, H2A, H2B, H3 and H4. However, this potent antibacterial mechanism occurs at the expense of injury to endothelium and tissue (Clark et al., 2007). The PI-positive staining of the endothelium upon exposure to NETs is similar to the inventors' finding that the endothelium could be damaged upon exposure to histones. Together with the increase of the histone in the circulation of *E. coli* challenged baboons, the lethal effect of histone injection and the rescuing effect of anti-histone H4 peptide in LPS-induced septic shock, the inventors propose that extracellular histones are major contributors to cellular dysfunction, subsequent organ failure and death.

APC is currently the only drug for the treatment of severe sepsis. The inventors now propose that destruction of cytotoxic histones as an additional mechanism by which APC exerts protective effects in septic patients. The protection of acute renal dysfunction by exogenous APC in baboons challenged with a lethal dose *E. coli* is consistent with the recent finding in which acquired protein C deficiency correlated with renal dysfunction in a cecal ligation and puncture model of polymicrobial sepsis and treatment with APC improved renal function and markers of tissue injury (Gupta et al., 2007). Whether histones are causative mediators in the renal dysfunction in sepsis and other renal diseases remains an open question. For example, in systemic lupus erythematosus (SLE), APC generation and binding onto phospholipids is often compromised by auto-immune antibodies against the components involved in the protein C pathway (Esmon et al., 2000). Given the enhancement of APC cleaving histones, as well as factor Va by PE containing lipids, anti-phospholipid antibodies may not only inhibit APC anti-coagulant activity but may also compromise the destruction of cytotoxic histones by APC and contribute to the severity of the disease. In human SLE patients, glomerular apoptotic nucleosomes are detected as central target structures for nephritogenic antibodies (Kalaaji et al., 2007), implying that extracellular histones could be involved in this pathogenic process.

I. HYPER-INFLAMMATORY DISEASE STATES

The present invention contemplates diagnosing and intervening in a variety of disease states that involve the release of histones and the resulting extracellular toxicity therefrom. A number of these disease states are described below.

A. Sepsis

Sepsis is a serious medical condition characterized by a whole-body inflammatory state caused by infection. Traditionally the term sepsis has been used interchangeably with septicaemia and septicemia ("blood poisoning"). However, these terms are no longer considered synonymous; septicemia is considered a subset of sepsis.

Symptoms of sepsis are often related to the underlying infectious process. When the infection crosses into sepsis, the resulting symptoms are that of systemic inflammatory response syndrome (SIRS): general inflammation, fever, elevated white blood cell count (leukocytosis), and raised heart rate (tachycardia) and breathing rate (tachypnea). Secondary to the above, symptoms also include flu like chills.

The immunological response that causes sepsis is a systemic inflammatory response causing widespread activation of inflammation and coagulation pathways. This may progress to dysfunction of the circulatory system and, even under optimal treatment, may result in the multiple organ dysfunction syndrome and eventually death.

Sepsis is considered present if infection is highly suspected or proven and two or more of the following systemic inflammatory response syndrome (SIRS) criteria are met:
heart rate >90 beats per minute
body temperature <36 (96.8° F.) or >38° C. (100.4° F.)
hyperventilation (high respiratory rate) >20 breaths per minute or, on blood gas, a $P_aCO_2$ less than 32 mm Hg
white blood cell count <4000 cells/mm$^3$ or >12000 cells/mm$^3$ (<4×10$^9$ or >12×10$^9$ cells/L), or greater than 10% band forms (immature white blood cells).
Consensus definitions however continue to evolve with the latest expanding the list of signs and symptoms of sepsis to reflect clinical bedside experience.

The more critical subsets of sepsis are severe sepsis (sepsis with acute organ dysfunction) and septic shock (sepsis with refractory arterial hypotension). Alternatively, when two or more of the systemic inflammatory response syndrome criteria are met without evidence of infection, patients may be diagnosed simply with "SIRS." Patients with SIRS and acute organ dysfunction may be termed "severe SIRS."

Patients are defined as having "severe sepsis" if they have sepsis plus signs of systemic hypoperfusion; either end organ dysfunction or a serum lactate greater than 4 mmol/dL. Patient are defined as having septic shock if they have sepsis plus hypotension after an appropriate fluid bolus (typically 20 ml/kg of crystalloid). The criteria for diagnosing an adult with sepsis do not apply to infants under one month of age. In infants, only the presence of infection plus a "constellation" of signs and symptoms consistent with the systemic response to infection are required for diagnosis.

The therapy of sepsis rests on antibiotics, surgical drainage of infected fluid collections, fluid replacement and appropriate support for organ dysfunction. This may include hemodialysis in kidney failure, mechanical ventilation in pulmonary dysfunction, transfusion of blood products, and drug and fluid therapy for circulatory failure. Ensuring adequate nutrition, if necessary by parenteral nutrition, is important during prolonged illness.

A problem in the adequate management of septic patients has been the delay in administering therapy after sepsis has been recognized. Published studies have demonstrated that for every hour delay in the administration of appropriate antibiotic therapy there is an associated 7% rise in mortality. A large international collaboration was established to educate people about sepsis and to improve patient outcomes with sepsis, entitled the "Surviving Sepsis Campaign." The Campaign has published an evidence-based review of management strategies for severe sepsis, with the aim to publish a complete set of guidelines in subsequent years.

Most therapies aimed at the inflammatory process itself have failed to improve outcome, however drotrecogin alfa (activated protein C, one of the coagulation factors) has been shown to decrease mortality from about 31% to about 25% in severe sepsis. To qualify for drotrecogin alfa, a patient must have severe sepsis or septic shock with an APACHE II score of 25 or greater and a low risk of bleeding. Low dose hydrocortisone treatment has shown promise for septic shock patients with relative adrenal insufficiency as defined by ACTH stimulation testing.

Standard treatment of infants with suspected sepsis consists of supportive care, maintaining fluid status with intravenous fluids, and the combination of a beta-lactam antibiotic (such as ampicillin) with an aminoglycoside such as gentamicin.

B. Trauma

Physical trauma is a serious and body-altering physical injury, such as the removal of a limb. Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to subsequent infection, including sepsis. The present invention provides to treatment of trauma, including both pre-treatment (in the case of a medical procedure) and treatment after trauma injury as occurred.

i. Surgery

Surgery uses operative manual and instrumental techniques on a patient to investigate and/or treat a pathological condition such as disease or injury, to help improve bodily function or appearance, or sometimes for some other reason.

The present invention can address trauma resulting from surgeries, as defined further below.

As a general rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anesthesia, antiseptic conditions, typical surgical instruments, and suturing or stapling. All forms of surgery are considered invasive procedures; so-called non-invasive surgery usually refers to an excision that does not penetrate the structure being addressed (e.g., laser ablation of the cornea) or to a radiosurgical procedure (e.g., irradiation of a tumor). Surgery can last from minutes to hours.

Surgical procedures are commonly categorized by urgency, type of procedure, body system involved, degree of invasiveness, and special instrumentation. Elective surgery is done to correct a non-life-threatening condition, and is carried out at the patient's request, subject to the surgeon's and the surgical facility's availability. Emergency surgery is surgery which must be done quickly to save life, limb, or functional capacity. Exploratory surgery is performed to aid or confirm a diagnosis. Therapeutic surgery treats a previously diagnosed condition.

Amputation involves cutting off a body part, usually a limb or digit. Replantation involves reattaching a severed body part. Reconstructive surgery involves reconstruction of an injured, mutilated, or deformed part of the body. Cosmetic surgery is done to improve the appearance of an otherwise normal structure. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

When surgery is performed on one organ system or structure, it may be classed by the organ, organ system or tissue involved. Examples include cardiac surgery (performed on the heart), gastrointestinal surgery (performed within the digestive tract and its accessory organs), and orthopedic surgery (performed on bones and/or muscles).

Minimally invasive surgery involves smaller outer incision(s) to insert miniaturized instruments within a body cavity or structure, as in laparoscopic surgery or angioplasty. By contrast, an open surgical procedure requires a large incision to access the area of interest. Laser surgery involves use of a laser for cutting tissue instead of a scalpel or similar surgical instruments. Microsurgery involves the use of an operating microscope for the surgeon to see small structures. Robotic surgery makes use of a surgical robot, such as Da Vinci or Zeus surgical systems, to control the instrumentation under the direction of the surgeon.

ii. Traumatic Hemorrhage

Traumatic hemorrhage accounts for much of the wide ranging international impact of injury, causing a large proportion of deaths and creating great morbidity in the injured. Despite differences in pre-hospital care, the acute management of traumatic hemorrhage is similar around the world and follows well accepted published guidelines. A critically injured patient's care occurs as four, often overlapping segments: the resuscitative, operative, and critical care phases. The diagnosis and control of bleeding should be a high priority during all of the phases of trauma care and is especially important in the patient who is in hemorrhagic shock. Early attempts at hemorrhage control include direct control of visible sources of severe bleeding with direct pressure, pressure dressings, or tourniquets; stabilization of long bone and pelvic fractures; and keeping the patient warm. During the resuscitative phase, warmed intravenous fluids, hypotensive resuscitation prior to surgical control of hemorrhage, and appropriate transfusion of blood and blood products are provided. In the operative phase, surgical control of the hemorrhage and any other injury, and additional transfusion is provide. Finally, the critical care phase provides for post-operative support and tissue perfusion.

C. Acute Pancreatitis

Acute pancreatitis is rapidly-onset inflammation of the pancreas. Depending on its severity, it can have severe complications and high mortality despite treatment. While mild cases are often successfully treated with conservative measures or laparoscopy, severe cases require invasive surgery (often more than one intervention) to contain the disease process.

D. Acute Respiratory Distress Syndrome

Acute respiratory distress syndrome (ARDS), also known as respiratory distress syndrome (RDS) or adult respiratory distress syndrome (in contrast with IRDS) is a serious reaction to various forms of injuries to the lung. This is the most important disorder resulting in increased permeability pulmonary edema.

ARDS is a severe lung disease caused by a variety of direct and indirect insults. It is characterized by inflammation of the lung parenchyma leading to impaired gas exchange with concomitant systemic release of inflammatory mediators causing inflammation, hypoxemia and frequently resulting in multiple organ failure. This condition is life threatening and often lethal, usually requiring mechanical ventilation and admission to an intensive care unit. A less severe form is called acute lung injury (ALI).

ARDS can occur within 24 to 48 hours of an injury or attack of acute illness. In such a case the patient usually presents with shortness of breath, tachypnea, and symptoms related to the underlying cause, i.e., shock. Long term illnesses can also trigger it, such as malaria. The ARDS may then occur sometime after the onset of a particularly acute case of the infection.

An arterial blood gas analysis and chest X-ray allow formal diagnosis by inference using the aforementioned criteria. Although severe hypoxemia is generally included, the appropriate threshold defining abnormal $PaO_2$ has never been systematically studied. Any cardiogenic cause of pulmonary edema should be excluded. This can be done by placing a pulmonary artery catheter for measuring the pulmonary artery wedge pressure. However, this is not necessary and is now rarely done as abundant evidence has emerged demonstrating that the use of pulmonary artery catheters does not lead to improved patient outcomes in critical illness including ARDS. Plain chest X-rays are sufficient to document bilateral alveolar infiltrates in the majority of cases. While CT scanning leads to more accurate images of the pulmonary parenchyma in ARDS, its has little utility in the clinical management of patients with ARDS, and remains largely a research tool.

Acute respiratory distress syndrome is usually treated with mechanical ventilation in the Intensive Care Unit. Ventilation is usually delivered through oro-tracheal intubation, or tracheostomy whenever prolonged ventilation (≥2 weeks) is deemed inevitable. The possibilities of non-invasive ventilation are limited to the very early period of the disease or, better, to prevention in individuals at risk for the development of the disease (atypical pneumonias, pulmonary contusion, major surgery patients). Treatment of the underlying cause is imperative, as it tends to maintain the ARDS picture. Appropriate antibiotic therapy must be administered as soon as microbiological culture results are available. Empirical therapy may be appropriate if local microbiological surveillance is efficient. More than 60% ARDS patients experience a (nosocomial) pulmonary infection either before or after the onset of lung injury. The origin of infection, when surgically treatable, must be operated on. When sepsis is diagnosed, appropriate local protocols should be enacted.

E. Ischemia-Reperfusion Injury

Reperfusion injury refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

The damage of reperfusion injury is due in part to the inflammatory response of damaged tissues. White blood cells carried to the area by the newly returning blood release a host of inflammatory factors such as interleukins as well as free radicals in response to tissue damage[1]. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. Leukocytes may also build up in small capillaries, obstructing them and leading to more ischemia.

Reperfusion injury plays a part in the brain's ischemic cascade, which is involved in stroke and brain trauma. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

In prolonged ischemia (60 min or more), hypoxanthine is formed as breakdown product of ATP metabolism. The enzyme xanthine dehydrogenase is converted to xanthine oxidase as a result of the higher availability of oxygen. This oxidation results in molecular oxygen being converted into highly reactive superoxide and hydroxyl radicals. Xanthine oxidase also produces uric acid, which may act as both a prooxidant and as a scavenger of reactive species such as peroxinitrite. Excessive nitric oxide produced during reperfusion reacts with superoxide to produce the potent reactive species peroxynitrite. Such radicals and reactive oxygen species attack cell membrane lipids, proteins, and glycosaminoglycans, causing further damage. They may also initiate specific biological processes by redox signaling.

F. Cardiovascular Disease

Cardiovascular disease refers to the class of diseases that involve the heart or blood vessels (arteries and veins). While the term technically refers to any disease that affects the cardiovascular system, it is usually used to refer to those related to atherosclerosis (arterial disease). These conditions have similar causes, mechanisms, and treatments. Treatment of cardiovascular disease depends on the specific form of the disease in each patient, but effective treatment always includes preventive lifestyle changes discussed above. Medications, such as blood pressure reducing medications, aspirin and the statin cholesterol-lowering drugs may be helpful. In some circumstances, surgery or angioplasty may be warranted to reopen, repair, or replace damaged blood vessels Most Western countries face high and increasing rates of cardiovascular disease. Each year, heart disease kills more Americans than cancer. Diseases of the heart alone caused 30% of all deaths, with other diseases of the cardiovascular system causing substantial further death and disability. Up until the year 2005, it was the number 1 cause of death and disability in the United States and most European countries. A large histological study (PDAY) showed vascular injury accumulates from adolescence, making primary prevention efforts necessary from childhood.

Some biomarkers are thought to offer a more detailed risk of cardiovascular disease. However, the clinical value of these biomarkers is questionable. Currently, biomarkers which may reflect a higher risk of cardiovascular disease include:

higher fibrinogen and PAI-1 blood concentrations
elevated homocysteine, or even upper half of normal
elevated blood levels of asymmetric dimethylarginine
high inflammation as measured by C-reactive protein
elevated blood levels of B-type natriuretic peptide (BNP)

Various forms of cardiovascular disease include aneurysms, angina, arrhythmia, atherosclerosis, cardiomyopathy, cerebrovascular disease, congenital heart disease, congestive heart failure, myocarditis, valve disease, coronary artery disease, dilated cardiomyopathy, diastolic dysfunction, endocarditis, high blood pressure (hypertension), hypertrophic cardiomyopathy, nitral valve prolapse, myocardial infarction, and venous thromboembolism.

G. Autoimmune/Inflammatory Disease

The present invention contemplates the treatment of a variety of autoimmune and/or inflammatory disease states such as spondyloarthropathy, ankylosing spondylitis, psoriatic arthritis, reactive arthritis, enteropathic arthritis, ulcerative colitis, Crohn's disease, irritable bowel disease, rheumatoid arthritis, juvenile rheumatoid arthritis, familial Mediterranean fever, amyotrophic lateral sclerosis, Sjogren's syndrome, early arthritis, viral arthritis, multiple sclerosis, or psoriasis. The diagnosis and treatment of these diseases are well documented in the literature.

H. Chemotherapy, Radiotherapy and Cytokine Therapy Toxicity

Various forms of cancer therapy, including chemotherapy, radiation, and cytokines, are associated with toxicity, sometimes severe, in the cancer patient. To the extent that the toxicity is caused at least in part by the extracellular actions of histones, the present invention seeks to reduce this toxicity using the pharmaceutical compositions of the present invention, thereby reducing or alleviating discomfort on the part of the patient, as well as permitting higher doses of the therapy.

I. Burns

In medicine, a burn may be an injury caused by heat, cold, electricity, chemicals, friction or radiation. First-degree burns are usually limited to redness (erythema), a white plaque, and minor pain at the site of injury. These burns usually extend only into the epidermis. Second-degree burns additionally fill with clear fluid, have superficial blistering of the skin, and can involve more or less pain depending on the level of nerve involvement. Second-degree burns involve the superficial (papillary) dermis and may also involve the deep (reticular) dermis layer. Third-degree burns additionally have charring of the skin, and produce hard, leather-like eschars. An eschar is a scab that has separated from the unaffected part of the body. Frequently, there is also purple fluid. These types of burns are often painless, because nerve endings have been destroyed in the burned areas. Serious burns, especially if they cover large areas of the body, can cause death; any hint of burn injury to the lungs (e.g., through smoke inhalation) is a medical emergency.

Burns that injure the tissues underlying the skin, such as the muscles or bones, are sometimes categorized as fourth-degree burns. These burns are broken down into three additional degrees: fourth-degree burns result in the skin being irretrievably lost, fifth-degree burns result in muscle being irretrievably lost, and sixth-degree burns result in bone being charred.

A newer classification of "Superficial Thickness," "Partial Thickness" (which is divided into superficial and deep categories) and "Full Thickness" relates more precisely to the epidermis, dermis and subcutaneous layers of skin and is used to guide treatment and predict outcome.

Chemical burns are usually caused by chemical compounds, such as sodium hydroxide (lye), silver nitrate, and more serious compounds (such as sulfuric acid). Most chemicals (but not all) that can cause moderate to severe chemical burns are strong acids or bases. Nitric acid, as an oxidizer, is possibly one of the worst burn-causing chemicals. Hydrofluoric acid can eat down to the bone and its burns are often not immediately evident. Most chemicals that can cause moderate to severe chemical burns are called caustic.

Electrical burns are generally symptoms of electric shock, being struck by lightning, being defibrillated or cardioverted without conductive gel, etc. The internal injuries sustained may be disproportionate to the size of the "burns" seen—as these are only the entry and exit wounds of the electrical current.

Burns are assessed in terms of total body surface area (TBSA), which is the percentage affected by partial thickness or full thickness burns (superficial thickness burns are not counted). The rule of nines is used as a quick and useful way to estimate the affected TBSA. The first step in managing a person with a burn is to stop the burning process. With dry powder burns, the powder should be brushed off first. With other burns, the affected area should be rinsed with a large amount of clean water to remove foreign bodies and help stop the burning process. Cold water should never be applied to any person with extensive burns, as it may severely compromise the burn victim's temperature status. At this stage of management, it is also critical to assess the airway status. If the patient was involved in a fire, then it must be assumed that he or she has sustained inhalation injury until proven otherwise, and treatment should be managed accordingly.

Once the burning process has been stopped, and airway status is ensured, the patient should be volume resuscitated according to the Parkland formula. This formula dictates that the amount of Lactated Ringer's solution to deliver in the first twenty four hours after time of injury is:

fluid=4 cc×% TBSA×weight in kg

% TBSA excludes any first degree burn
Half of this fluid should be given in the first eight hours post injury and the rest in the subsequent sixteen hours. The formula is a guide only and infusions must be tailored to urine output and central venous pressure. Inadequate fluid resuscitation causes renal failure and death. Severe edema in full thickness burns may be treated by escharotomy.

II. HISTONES

A. General Information

In biology, histones are the chief protein components of chromatin. They act as spools around which DNA winds, and they play a role in gene regulation. Six major histone classes are known: H1 (sometimes called the linker histone; also related to Histone H5); H2A; H2B; H3; H4; and archaeal histones. Two each of the class H2A, H2B, H3 and H4, so-called core histones, assemble to form one octameric nucleosome core particle by wrapping 146 base pairs of DNA around the protein spool in 1.65 left-handed superhelical turn. The linker histone H1 binds the nucleosome and the entry and exit sites of the DNA, thus locking the DNA into place and allowing the formation of higher order structure. The most basic such formation is the 10 nm fiber or beads on a string conformation. This involves the wrapping of DNA around nucleosomes with approximately 50 base pairs of DNA spaced between each nucleosome (also referred to as linker DNA). The assembled histones and DNA is called chromatin. Higher order structures include the 30 nm fiber (forming an irregular zigzag) and 100 nm fiber, these being the structures found in normal cells. During mitosis and meiosis, the condensed chromosomes are assembled through interactions between nucleosomes and other regulatory proteins.

The nucleosome core is formed of two H2A-H2B dimers and a H3-H4 tetramer, forming two nearly symmetrical halves by tertiary structure (C2 symmetry; one macromolecule is the mirror image of the other). The H2A-H2B dimers and H3-H4 tetramer also show pseudodyad symmetry. The 4 core histones (H2A, H2B, H3 and H4) are relatively similar in structure and are highly conserved through evolution, all featuring a "helix-turn-helix-turn-helix" motif (which allows the easy dimerization). They also share the feature of long tails on one end of the amino acid structure—this being the location of post-transcriptional modification.

In all, histones make five types of interactions with DNA: (a) helix-dipoles from alpha-helices in H2B, H3, and H4 cause a net positive charge to accumulate at the point of interaction with negatively charged phosphate groups on DNA; (b) hydrogen bonds between the DNA backbone and the amine group on the main chain of histone proteins; (c) nonpolar interactions between the histone and deoxyribose sugars on DNA; (d) salt links and hydrogen bonds between side chains of basic amino acids (especially lysine and arginine) and phosphate oxygens on DNA; and non-specific minor groove insertions of the H3 and H2B N-terminal tails into two minor grooves each on the DNA molecule.

The highly basic nature of histones, aside from facilitating DNA-histone interactions, contributes to the water solubility of histones. Histones are subject to post-translational modification by enzymes primarily on their N-terminal tails, but also in their globular domains.

Such modifications include methylation, citrullination, acetylation, phosphorylation, sumoylation, ubiquitination, and ADP-ribosylation. This affects their function of gene regulation.

In general, genes that are active have less bound histone, while inactive genes are highly associated with histones during interphase. It also appears that the structure of histones have been evolutionarily conserved, as any deleterious mutations would be severely maladaptive.

As stated above, histones act as spools around which DNA winds. This enables the compaction necessary to fit the large genomes of eukaryotes inside cell nuclei: the compacted molecule is 50,000 times shorter than an unpacked molecule Histones undergo posttranslational modifications which alter their interaction with DNA and nuclear proteins. The H3 and H4 histones have long tails protruding from the nucleosome which can be covalently modified at several places. Modifications of the tail include methylation, acetylation, phosphorylation, ubiquitination, sumoylation, citrullination, and ADP-ribosylation. The core of the histones (H2A and H3) can also be modified. Combinations of modifications are thought to constitute a code, the so-called "histone code." Histone modifications act in diverse biological processes such as gene regulation, DNA repair and chromosome condensation (mitosis).

The common nomenclature of histone modifications is as follows: the name of the histone (e.g., H3); the single letter amino acid abbreviation (e.g., K for Lysine) and the amino acid position in the protein; and the type of modification (Me: methyl, P: phosphate, Ac: acetyl, Ub: ubiquitin). So H3K4Me denotes the methylation of H3 on the 4th lysine from the start (N-terminal) of the protein.

B. Histone Peptides mRNA accession nos. for human histones, each of which are incorporated herein by reference, are as follows: H1 (NM_005318), H2A (NM_001017990), H2B (XM_210048), H3 (A-NM_002107 and B-NM_005324) and H4 (X00038.1).

The present invention contemplates the use of peptides and fragments of histones for generation of antibodies and for use as therapeutic compositions in the treatment of hyper-inflammatory disorders. Histone peptides will comprise molecules of 4 to about 50 residues in length. A particular length may be less than 35 residues, less than 30 residues, less than 25 residues, less than 20 residues, less than 15 residues, or less than 13, including 6, 7, 8, 9, 10, 11, 12, 13, 14, 15, 16, 17, 18, 19 or 20 residues. The peptides may be generated synthetically or by recombinant techniques, and are purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

The peptides may be labeled using various molecules, such as fluorescent, chromogenic or colorimetric agents. The peptides may also be linked to other molecules, including other anti-inflammatory agents. The links may be direct or through distinct linker molecules. The linker molecules in turn may be subject, in vivo, to cleavage, thereby releasing the agent from the peptide. Peptides may also be rendered multimeric by linking to larger, and possibly inert, carrier molecules.

It also is contemplated in the present invention that variants or analogs of histone peptides may block histone cytotoxicity. Polypeptide sequence variants of histones, primarily making conservative amino acid substitutions, may provide improved compositions. Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a peptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a peptide that defines that peptide's biological functional activity, certain amino acid substitutions can be made in a protein sequence, and its underlying DNA coding sequence, and nevertheless obtain a peptide with like properties. It is thus contemplated by the inventors that various changes may be made in the DNA sequences coding the peptide without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant peptide, which in turn defines the interaction of the peptide with other molecules.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a peptide with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine*−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide containing molecules that mimic elements of protein secondary structure (Johnson et al, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of MBPs, but with altered and even improved characteristics.

The present invention also may employ peptides that comprise modified, non-natural and/or unusual amino acids. Table 1 provides exemplary, but not limiting, modified, non-natural and/or unusual amino acids is provided herein below. Chemical synthesis may be employed to incorporated such amino acids into the peptides of interest.

TABLE 1

Modified, Non-Natural and Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In addition to the variants discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents. Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains. Beta II turns have been mimicked successfully using cyclic L-pentapeptides and those with D-amino acids (Weisshoff et al., 1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally-restricted β turns and β bulges are described, for example, in U.S. Pat. Nos. 5,440,013; 5,618,914; and 5,670,155. β-turns permit changed side substituents without having changes in corresponding backbone conformation, and have appropriate termini for incorporation into peptides by standard synthesis procedures. Other types of mimetic turns include reverse and γ turns. Reverse turn mimetics are disclosed in U.S. Pat. Nos. 5,475,085 and 5,929,237, and γ turn mimetics are described in U.S. Pat. Nos. 5,672,681 and 5,674,976.

C. Fusions

Another variant is a fusion. This molecule generally has all or a substantial portion of the original molecule, in this case a peptide comprising a histone sequence, linked at the N- or C-terminus to all or a portion of a second peptide or polypeptide. For example, fusions may employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

D. Purification of Proteins

It may be desirable to purify peptides, fragments, peptidemimics or analogs thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from claims and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

E. Peptide Synthesis

Histone-related peptides may be generated synthetically for use in various embodiments of the present invention. Because of their relatively small size, the peptides of the invention can be synthesized in solution or on a solid support in accordance with conventional techniques. Various automatic synthesizers are commercially available and can be used in accordance with known protocols. See, for example, Stewart & Young, (1984); Tam et al., (1983); Merrifield, (1986); Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

III. ANTIBODIES AND IMMUNOASSAYS

It will be understood that polyclonal or monoclonal antibodies that bind immunologically to histones will have use in several applications. These include diagnostic kits and methods of detecting histones, as well as therapeutic intervention. Means for preparing and characterizing antibodies are well known in the art (see, e.g., Antibodies: A Laboratory Manual, 1988; incorporated herein by reference). The term "antibody" as used herein is used to refer to any antibody-like molecule that has an antigen binding region, and includes antibody fragments such as Fab', Fab, F(ab')2, single domain antibodies (DAB's), Fv, scFv (single-chain Fv), and the like.

A. Polyclonal Antisera

Polyclonal antisera is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimido-bencoyl-N-hydroxysuccinimide ester, carbodiimyde and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, also may be given. The process of boosting and titering is repeated until a suitable titer is achieved. When a desired level of immunogenicity is obtained, the immunized animal can be bled and the serum isolated and stored, or the animal can be used to generate mAbs (below).

For production of rabbit polyclonal antibodies, the animal can be bled through an ear vein or alternatively by cardiac puncture. The procured blood is allowed to coagulate and then centrifuged to separate serum components from whole cells and blood clots. The serum may be used as is for various applications or else the desired antibody fraction may be purified by well-known methods, such as affinity chromatography using another antibody or a peptide bound to a solid matrix or protein A followed by antigen (peptide) affinity column for purification.

B. Monoclonal Antibodies mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified histones, fragments or peptides therefrom. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep, goat, monkey cells also is possible. The use of rats may provide certain advantages (Goding, 1986, pp. 60-61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens or lymph nodes. Spleen cells and lymph node cells are preferred, the former because they are a rich source of antibody-producing cells that are in the dividing plasmablast stage.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984; each incorporated herein by reference). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding pp. 71-74, 1986).

Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

A particular selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like. The selected hybridomas would then be serially diluted and cloned into individual antibody-producing cell lines, which clones can then be propagated indefinitely to provide mAbs. The cell lines may be exploited for mAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide mAbs in high concentration.

The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

C. Immunoassays

The present invention thus concerns immunodetection methods for binding, quantifying or otherwise generally detecting histones. The steps of various useful immunodetection methods have been described in the scientific literature, such as, e.g., Nakamura et al. (1987); incorporated herein by reference. Immunoassays, in their most simple and direct sense, are binding assays. Certain preferred immunoassays are the various types of enzyme linked immunosorbent assays (ELISAs), radioimmunoassays (RIA) and immunobead capture assay. However, it will be readily appreciated that detection is not limited to such techniques, and Western blotting, dot blotting, and the like also may be used in connection with the present invention.

In general, immunobinding methods include obtaining a sample suspected of containing a histone, fragment or peptide, and contacting the sample (such as blood, serum or plasma) with an antibody or protein or peptide in accordance with the present invention, as the case may be, under conditions effective to allow the formation of immunocomplexes.

The immunobinding methods of this invention include methods for detecting or quantifying the amount of a reactive component in a sample, which methods require the detection or quantitation of any immune complexes formed during the binding process. Here, one would obtain a sample suspected of containing extracellular histone, and contact the sample with an antibody, and then detect or quantify the amount of immune complexes formed under the specific conditions.

Contacting the chosen biological sample with the antibody or antisera under conditions effective and for a period of time sufficient to allow the formation of immune complexes (primary immune complexes) is generally a matter of simply adding the composition to the sample and incubating the mixture for a period of time long enough for the antibodies to form immune complexes with extracellular histones. After this time, the sample-antibody composition will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference.

In certain embodiments, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

Of particular interest in the present invention are enzyme linked immunosorbent assays, known as ELISAs. In one exemplary ELISA, antibodies binding to the encoded proteins of the invention are immobilized onto a selected surface exhibiting protein affinity, such as a well in a polystyrene microtiter plate. Then, a test composition suspected of containing the extracellular histones is added to the wells. After binding and washing to remove non-specifically bound immunocomplexes, the bound antigen may be detected.

Detection is generally achieved by the addition of a second antibody specific for the target protein, that is linked to a detectable label. This type of ELISA is a simple "sandwich ELISA." Detection also may be achieved by the addition of a second antibody, followed by the addition of a third antibody that has binding affinity for the second antibody, with the third antibody being linked to a detectable label.

In another exemplary ELISA, the samples suspected of containing the extracellular histones are immobilized onto the well surface and then contacted with the antibodies of the invention. After binding and washing to remove non-specifically bound immune complexes, the bound antibody is detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the extracellular histones are immobilized, involves the use of antibody competition in the detection. In this ELISA, labeled antibodies are added to the wells, allowed to bind to the extracellular histones and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immune complexes. For example, in coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is more customary to use a secondary or tertiary detection means rather than a direct procedure. Thus, after binding of a protein or antibody to the well, coating with a non-reactive material to reduce background, and washing to remove unbound material, the immobilizing surface is contacted with a control and sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hrs, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation (e.g., incubation for 2 hrs at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-3-ethyl-benzothiazoline-6-sulfonic acid (ABTS) and $H_2O_2$, in the case of peroxidase as the enzyme label. Quantitation is then achieved by measuring the degree of color generation, e.g., using a visible spectra spectrophotometer.

IV. DIAGNOSIS AND THERAPY

In certain aspects, the present invention relates to the diagnosis and treatment of hyper-inflammatory disorders that have as a component the production of cytotoxic amounts of extracellular histones. By using agents that cleave, bind and block the function of the extracellular histones, the inventors seek to reduce and inhibit the toxic effects of these molecules. In addition, the presence of such extracellular histones, alone or in conjunction with other diagnostic features, may identify subjects at risk of developing life-threatening hyper-inflammatory reactions. Thus, assays to detect extracellular histones in samples, such as blood, plasma and serum, also are proposed.

A. Diagnosis/Prognosis

In one aspect, the present invention will entail obtaining a biological sample from a patient at risk of or suspected of having a hyper-inflammatory condition involving extracellular histone production and toxicity. Biological samples will typically entail blood, plasma or serum, but other fluids such as saliva, sputum, and urine may be utilized. Employing the immunological assays described above, or other techniques (e.g., mass spectrometry such as MALDI-TOF), the histone content of the sample is assessed, with elevated levels of histones being indicative of a hyper-inflammatory disorder. The subject may then be treated, as discussed below, or simply monitored for further progression or recovery.

B. Therapies

The present invention contemplates the use of inhibitors of extracellular histone cytotoxicity to treat a variety of hyper-inflammatory disease states specified above. The inventors contemplate the use fragments/peptides from histones, particularly histones H3 and H4, as well as enzymes that cleave histones (APC, granzymes A & B), and antibodies to histones. Also contemplated are mixtures of these agents, including (a) at least one histone peptide, at least one anti-histone antibody, (b) multiple histone peptides, (c) multiple histone antibodies, and (d) a histone-cleaving enzyme and at least one histone peptide/and or anti-histone antibody. Of particular interest are peptides and antibodies that target H4, such as an H4 peptide representing residues 50-67 of H4 (SEQ ID NO: 19).

Treatment regimens will vary depending on the severity and type of disease, the overall health and age of the patient, and various other conditions to be taken into account by the treating physician. Multiple doses or treatments may be applied, as well as "continuous" therapy where a small amount of the therapeutic agent is provided continually over an extended period of time. The agent may also be provided in a single bolus administration, but is formulated to provided delayed, timed or extended release of the active form.

In addition, combinations of an inhibitor of extracellular histone cytotoxicity with other treatments may be used by administration of a single composition or pharmacological formulation that includes both multiple agents, or by administering two distinct compositions or formulations, at the same time. Alternatively, one treatment may precede or follow administration of the other by intervals ranging from minutes to weeks. In embodiments where the two agents are applied separately, one would generally ensure that a significant period of time did not expire between the time of each delivery, such that both agents would still be able to exert an advantageously combined effect. In such instances, it is contemplated that one would typically administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. It also is conceivable that more than one administration of a drug will be desired.

By way of illustration, the following permutations based on 3 and 4 total administrations are exemplary, where A represents a first inhibitor of extracellular histone cytotoxicity and B represents a second drug (including a second inhibitor of extracellular histone cytotoxicity):

| | | | | | | | |
|---|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are likewise contemplated.

C. Pharmaceutical Formulations and Routes for Administration to Patients

Where clinical applications are contemplated, pharmaceutical compositions including histone peptides, fragments and anti-histone antibodies, and mixtures thereof, will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intraarterial, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials & Methods

Materials.

Mouse protein C, bovine factor V, X and thrombin, rat anti-mouse EPCR (MEPCR1560) and mouse TM (MTM1703) were produced in this laboratory according to the standard procedures. Human recombinant APC (Xigris) was purchased from Eli Lilly. Calf thymus histones (Sigma), calf thymus histone H4 (Roche), LPS from *Salmonella*

*typhimurium* (Sigma), mouse recombinant IFN (Biosource), synthetic histone H4 peptides (GenScript), *E. coli* M15 strain (Qiagen) were also purchased. *E. coli* B7 strain was provided by Dr. F. B. Taylor.

Animals.

Six to 10-week male C57BL/6 mice (Jackson Lab) were used according to an animal protocol approved by Institutional Animal Care and Use Committees of the Oklahoma Medical Research Foundation.

Mouse Peritoneal Macrophage.

Mice were injected intraperitoneally with 2 ml 3% thioglycollate medium. Four days later peritoneal exudate cells were harvested by lavage with 10 ml cold HBSS containing 10 U/ml heparin. Peritoneal cells were washed once and resuspended in RPMI 1640 medium containing 10% fetal bovine serum (FBS), plated in 24-well plate and non-adherent cells were washed out after 2 hr cell culture. The adherent peritoneal macrophages were stimulated with 1 µg/ml LPS, 20 ng/ml mouse IFN or both for 24 hr. There were $0.8$-$1.0 \times 10^6$ cells/well with or without these treatments.

Cell Culture.

Mouse macrophage cell line RAW264.7 cells were cultured in RPMI 1640 medium supplemented with 10% FBS. Human endothelial EA.hy926 cells were cultured in DMEM supplemented with 10% FBS and HAT (hypoxanthine, aminopterin, thymidine).

Real Time PCR to Quantitate EPCR and TM mRNA Expression.

Total RNA was isolated from mouse tissue using TRIzol reagent (Invitrogen). cDNA was synthesized from total RNA by SuperScript First-Strand Synthesis System (Invitrogen). Real time PCR was carried out with SYBR Green PCR Core Reagents, ABI Prism 7000 Sequence Detection System (Applied Biosystems) and the following primers:

```
β-Actin:
                                   (SEQ ID NO: 1)
Forward: TGAGAGGGAAATCGTGCGTGAC (SEQ ID NO: 2)
Reverse: GAGGAAGAGGATGCGGCAGTG EPCR:
                                   (SEQ ID NO: 3)
Forward: CAGTTCGAAAGCCTGGTGAAG (SEQ ID NO: 4)
Reverse: GCAGCTAACAGTGAGAGGAAAGAA TM:
                                   (SEQ ID NO: 5)
Forward: GAAACTTCCCTGGCTCCTATGA (SEQ ID NO: 6)
Reverse: AGTCTTTGCTAATCTGACCAGCAA
```

Relative EPCR or TM mRNA expression level from each sample was determined after normalized with its β-Actin mRNA.

Immunoprecipitation and Western Blot of EPCR.

Mouse organ tissue was homogenized by extraction buffer (0.25 M sucrose, 20 mM Tris-HCl, pH 7.5, 1% Triton X-100) plus protease inhibitor cocktail (Roche) with PowerGen Homogenizer (Fisher Scientific), centrifuged at 16,000 g for 20 min at 4° C. The supernatant diluted to 10 mg protein in 1 ml with extraction buffer was immunoprecipited for EPCR by mixing with RMEPCR1560 Ab and Protein G Sepharose 4 fast flow resin (Amersham Biosciences) for 2 hr at 4° C. The immunoprecipitate was washed three times with cold TBS containing 0.1% Triton X-100, dissociated from Protein G resin after 5 min boiling with SDS-PAGE loading buffer, separated by SDS-PAGE, and Western blotted with biotin labeled RMEPCR1543 Ab, streptavidin-HRP and ECL system (Amersham Biosciences).

EPCR and TM Surface Expression Determined by Flow Cytometry.

Mouse peritoneal macrophages were stained with 10 µg/ml biotinylated MEPCR 1560 for mouse EPCR, biotinylated MTM 1703 for TM in the presence of 10 µg/ml anti-mouse CD16/32 in PBS containing 2% FBS, 0.1% NaN3 buffer for 30 min on ice, washed, and stained with 2 µg/ml PE-streptavidin for 30 min on ice, washed again and subjected to flow cytometry.

Protein C Activation on Mouse Macrophage.

Mouse peritoneal macrophages in 24-well plates were washed once with PBS and then added 0.2 ml DMEM containing 0.1% BSA, 10 nM bovine thrombin and 100 nM mouse protein C in the presence or absence of 200 nM MEPCR1560 mAb. After 30 min at 37° C., 50 µl supernatant was transferred to the 96 well microplate and mixed with 5 µl hirudin (5 mg/ml). The amidolytic activities of APC were measured with V. at 405 nm by adding 50 µl of 0.4 mM Spectrozyme Pca substrate in 0.1 M NaCl, 50 mM HEPES-HCl, pH 7.5 buffer. APC concentrations were determined by reference to a standard curve for purified mouse APC. For prothrombin and protein C activation assay, 200 nM bovine prothrombin, 3 nM bovine factor V and 85 nM bovine factor X were used instead of 10 nM bovine thrombin. Thrombin activities were determined by its amidolytic activity toward Spectrozyme thrombin substrate.

Western Blot of Histone H4 from Stimulated Macrophage Conditioned Medium.

RAW264.7 cells were stimulated with 1 µg/ml LPS and 20 ng/ml IFN for 24 hr, washed with PBS, and cultured in Opti-MEM medium (Invitrogen) with or without 100 nM human APC for 24 hr. The conditioned medium was filtered through a 0.22 µm filter and concentrated 80 fold with an Amicon Ultra 10,000 (Millipore). Concentrated conditioned medium was subject to SDS-PAGE and Western blotted with mouse monoclonal antibody against histone H4 (BWA-3).

Histone H4 Cleavage Sites Generated by APC.

0.1 mg/ml histone H4 was incubated with 20 µg/ml human APC in PBS containing 1 mM $CaCl_2$ and $MgCl_2$ at 37° C. for 60 min. Sample was subjected to SDS-PAGE and GelCode Blue (PIERCE) staining or sent to matrix-assisted laser desorption ionization-time of flight facility at the University of Oklahoma Health Science Center for molecular weight determination.

Histone Cytotoxicity Assay.

EA.hy926 cells were incubated with 50 µg/ml histones, histone H4 or histone H4 peptide (H4P39) in Opti-MEM medium at 37° C. for 60 min and then for 5 min at RT after 10 µg/ml propidium iodide (PI) was added. Cells were washed and detached with 0.526 mM EDTA in PBS and subjected to flow cytometry for PI (FL3) positive staining.

Bactericidal Activity Assay.

*E. coli* were incubated with 100 µg/ml histones, histone H4 or histone H4 peptide (H4P39) for 30 min at 37° C. with shaking in HBSS containing 10 mM HEPES, pH 7.5 and 0.3% trypticase soy broth. Samples were then plated on LB agar and incubated at 37° C. overnight. Bactericidal activity of histones, histone H4 and H4P39 was determined by comparing bacterial colony numbers on the plates.

Example 2—Results

Upregulation of EPCR and Protein C Activation on Macrophages Activated by LPS and IFN.

Figure 1B:
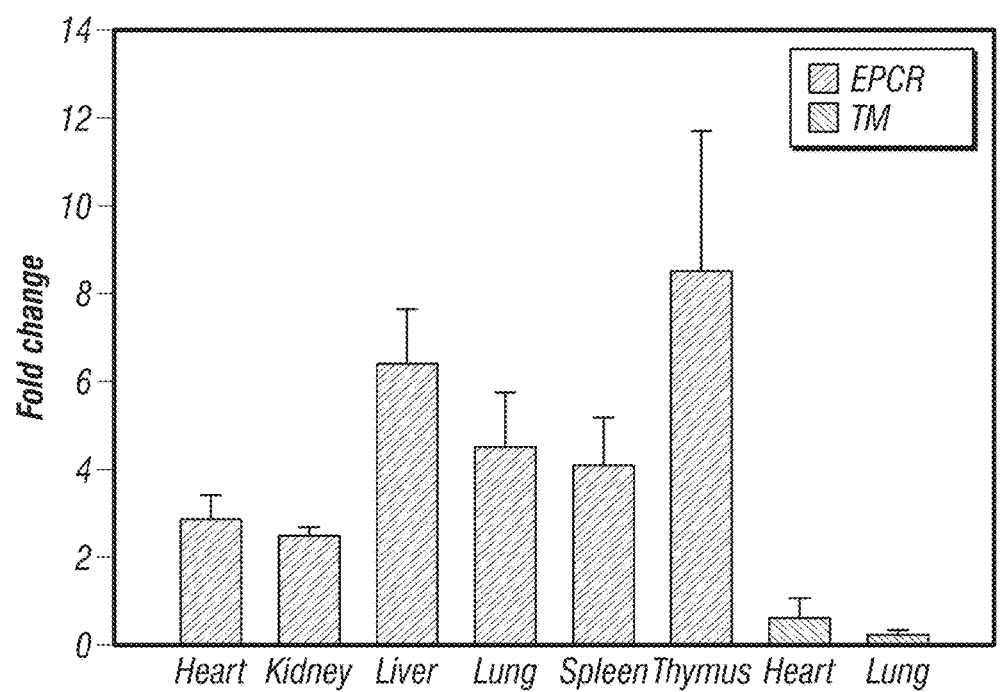
Figure 1C:
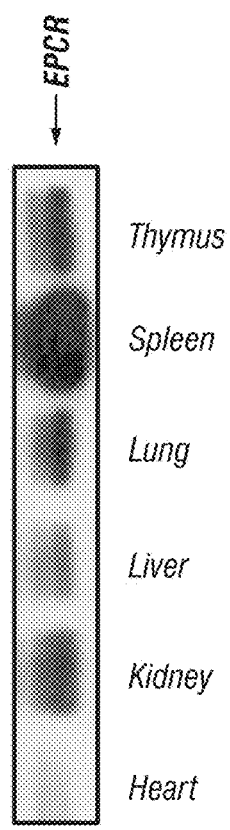

Unlike TM mRNA expression pattern which is highest in mouse lung tissue but low in heart, kidney, liver, spleen and thymus, EPCR mRNA is highly expressed in spleen and other organ tissues (FIG. 1A). In contrast to down regulation of TM mRNA in mouse lung and heart tissues, EPCR mRNA was up regulated by LPS challenge in all organ tissues we examined (FIG. 1B). Immunoprecipitation and Western blot confirmed that EPCR protein was highly expressed in spleen and other organ tissues (FIG. 1C). These results indicated that EPCR might be expressed on other cell types in addition to endothelial cells.

Figure 2A:
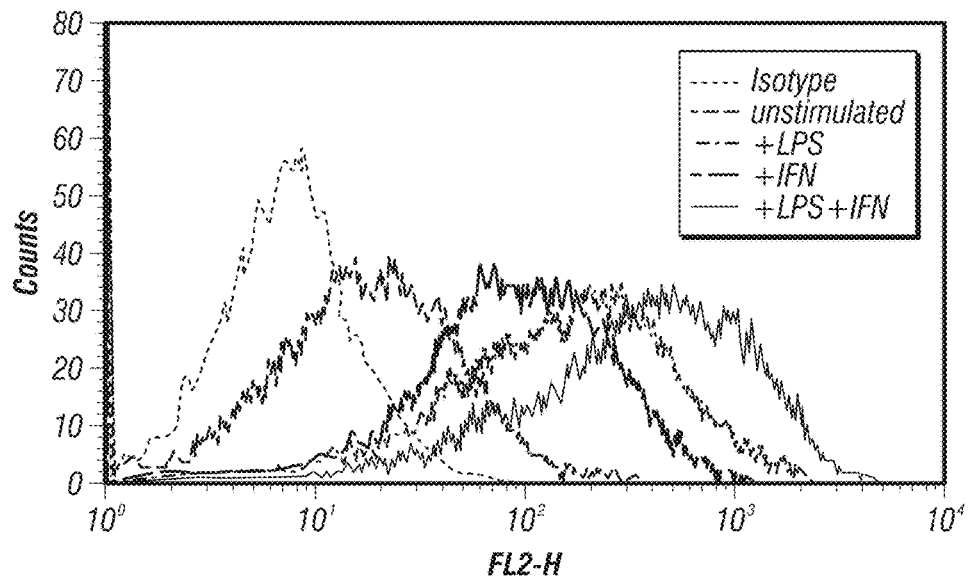
FIGS. 2A-B—Differential regulation of EPCR and TM on mouse macrophage by LPS and IFN. Mouse peritoneal macrophages were stimulated with LPS (1 µg/ml), IFN (20 ng/ml) or both for 24 hr.
Figure 2B:
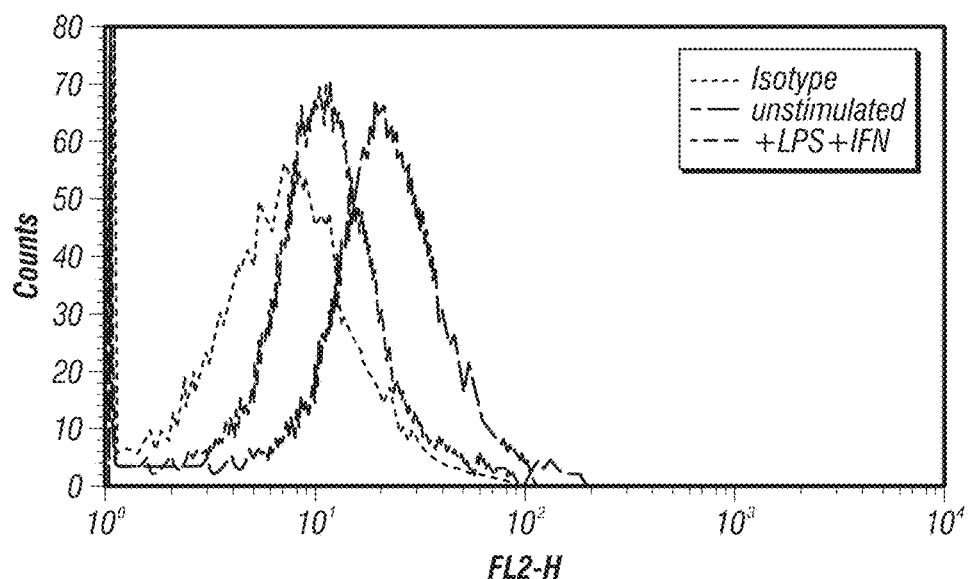
Figure 3A:
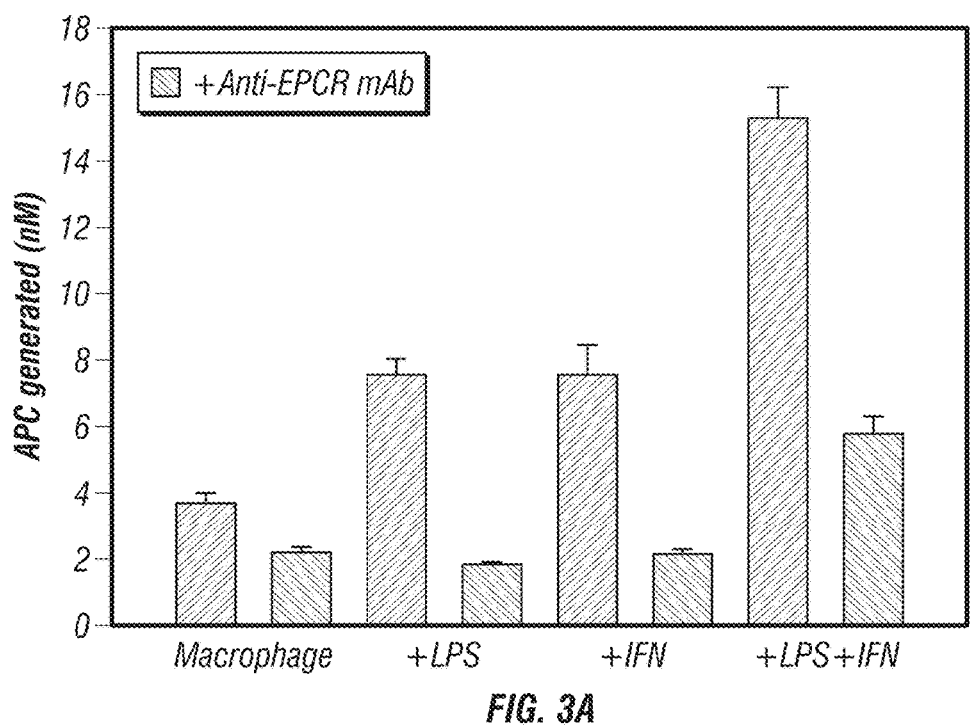
FIGS. 3A-C—Enhancement of protein C activation on activated macrophages by LPS and IFN.
Figure 3B:
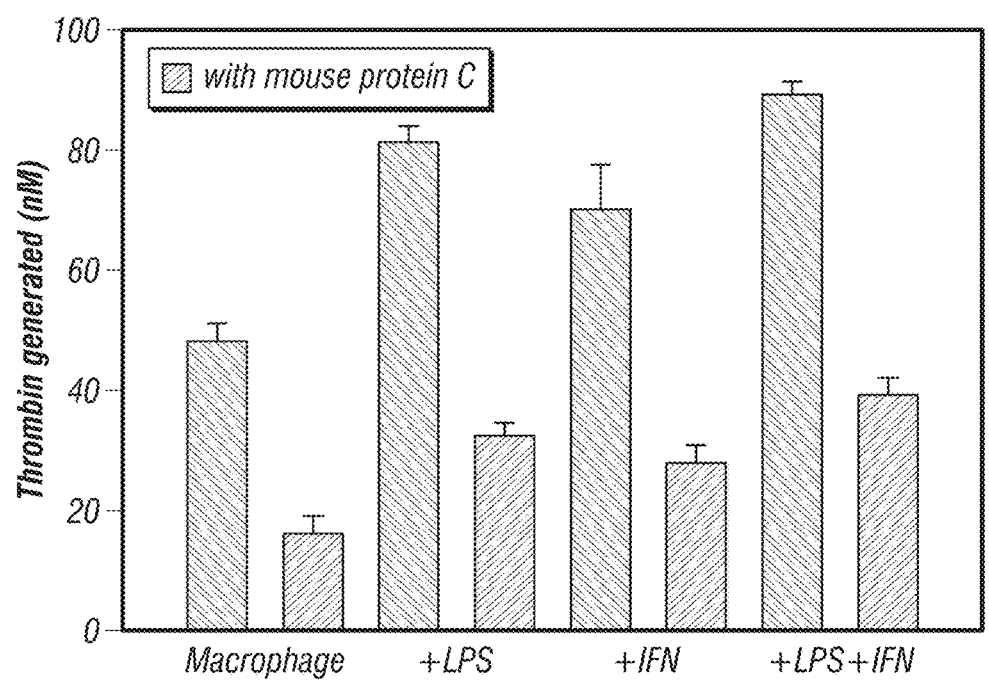
Figure 3C:
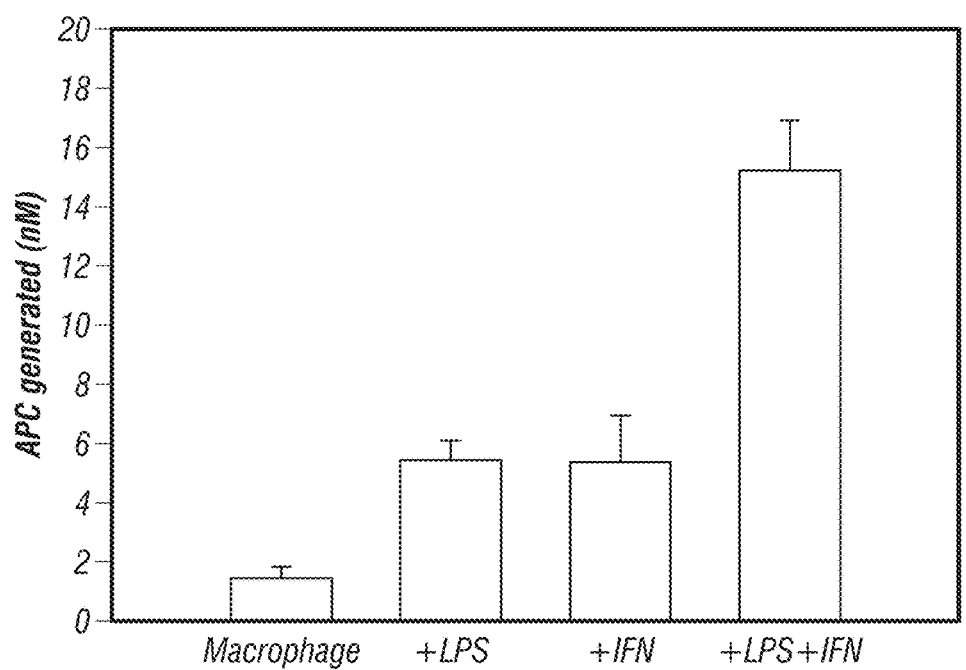

In the study of EPCR expression on various mouse immune cells, the inventors found that EPCR could be dramatically up regulated on peritoneal macrophages by LPS and IFN (FIG. 2A), in contrast to the down regulation of TM (FIG. 2B). EPCR mRNA was also greatly increased after LPS and IFN stimulation (data not shown), suggests that cell surface EPCR up-regulation is due to de novo protein synthesis. The inventors showed previously that EPCR could enhance protein C activation by thrombin-TM complex in a reconstituted liposome system in an EPCR concentration dependent fashion (10), and here we found that the enhancement of protein C activation on activated macrophages after LPS and IFN stimulation correlated to the EPCR expression level, EPCR monoclonal antibody could effectively inhibit protein C activation (FIG. 3A). Interestingly, mouse peritoneal macrophages constitutively express coagulation factor VII mRNA (data not shown), and when the inventors added coagulation factor V, X, prothrombin and protein C on these cells, both thrombin and APC could be easily detected (FIG. 3B), suggesting that initiation, amplification and stop of blood coagulation could happen on the same cell of macrophages with the endogenous tissue factor and coagulation factor VII. Again, the protein C activation under this circumstance was also greatly increased on activated macrophages stimulated with LPS and IFN (FIG. 3C). No prothrombin or protein C activation could be detected in the absence of factor V or X (data not shown).

APC Cleaves Histone H4 Released from Activated Macrophages.

Figure 4A:
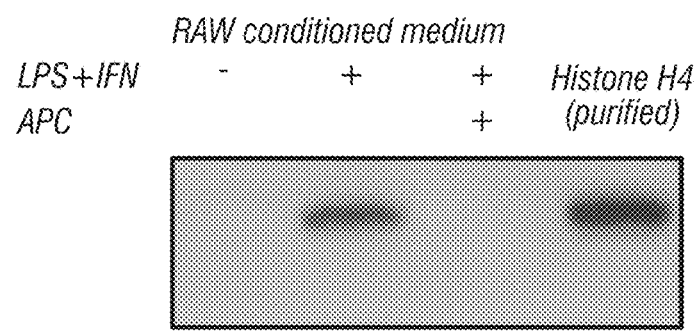
FIGS. 4A-B—APC cleaves histone H4.
Figure 4B:
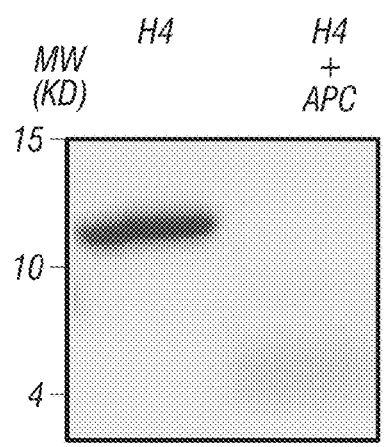

Next, the inventors asked whether APC could play any role on activated macrophages other than as an anticoagulant. They incubated LPS and IFN activated mouse macrophage RAW264.7 cells with recombinant human APC and found that histone H4 was released into the conditioned medium and was cleaved by APC (FIG. 4A). The epitope of mAb BWA3 used in the Western blot is in the N terminus of both histone H2A and histone H4 (Monestier et al., 1993). Only histone H4, but not histone H2A, was detected in this condition (FIG. 4A). Purified histone H4 was also cleaved by APC and a cluster of 4-7 KD fragments could be found on SDS-PAGE (FIG. 4B). Mass spectrum of these histone H4 fragments identified these peptide cleavage sites generated by APC (Table 2).

TABLE 2

Mass spectrum determines histone H4 cleavages sites generated by APC

| Obsv'd MW | Theoret. MW | Position | Peptide Sequence |
|---|---|---|---|
| 4473.27 | 4473.48 | 40-78 | RGGVKRISGLIYEETRGVLKVFLENVIRDAVTYTEHAKR (SEQ ID NO: 7) |
| 4969.62 | 4969.81 | 36-78 | RLARGGVKRISGLIYEETRGVLKVFLENVIRDAVTYTEHAKR (SEQ ID NO: 8) |
| 5098.13 | 5097.90 | 36-79 | RLARGGVKRISGLIYEETRGVLKVFLENVIRDAVTYTEHAKRK (SEQ ID NO: 9) |
| 5893.50 | 5893.26 | 40-91 | RGGVKRISGLIYEETRGVLKVFLENVIRDAVTYTEHAKRKTVTAMDVVYALK (SEQ ID NO: 10) |
| 6049.69 | 6049.37 | 40-92 | RGGVKRISGLIYEETRGVLKVFLENVIRDAVTYTEHAKRKTVTAMDVVYALKR (SEQ ID NO: 11) |
| 6390.96 | 6390.55 | 40-95 | RGGVKRISGLIYEETRGVLKVFLENVIRDAVTYTEHAKRKTVTAMDVVYALKRQGR (SEQ ID NO: 12) |
| 6545.55 | 6545.69 | 36-92 | RLARRGGVKRISGLIYEETRGVLKVFLENVIRDAVTYTEHAKRKTVTAMDVVYALKR (SEQ ID NO: 13) |

Cleaving Histone H4 by APC Modulates Histone H4 Bactericidal and Cytotoxic Activities.

Figure 5A:
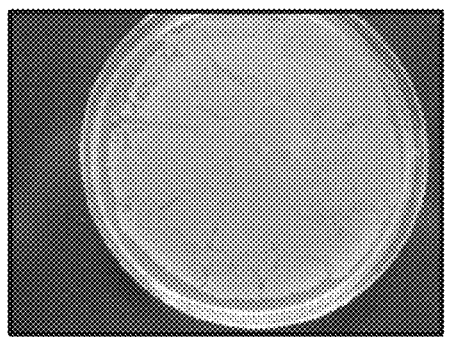
FIGS. 5A-C—APC modulates histone H4 antibacterial and cytotoxic activities. Histones, histone H4 or H4 peptide (H4P39) generated by APC were measured for their bactericidal activity against E. coli B7 strain (FIG. 5A) or M15 strain (FIG. 5B), and for their cytotoxic activity toward EA.hy926 endothelial cells by PI staining (FIG. 5C).
Figure 5A:
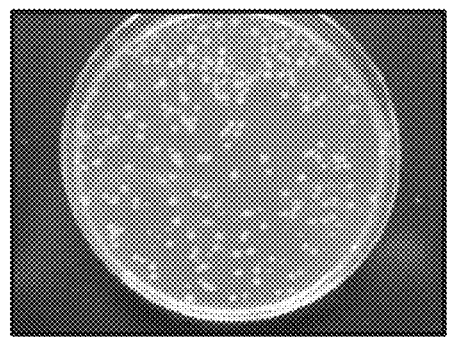
Figure 5A:
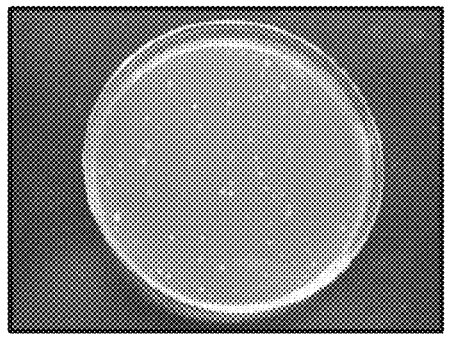
Figure 5A:
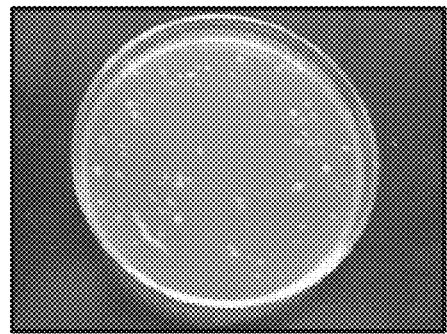
Figure 5B:
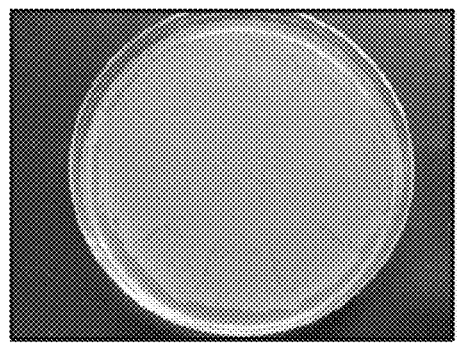
Figure 5B:
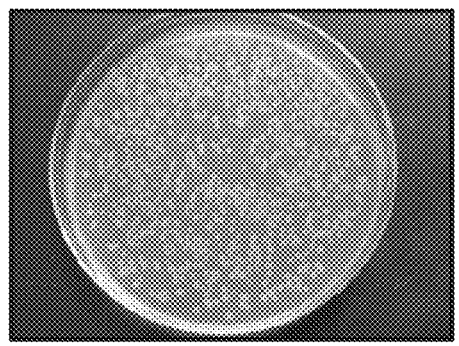
Figure 5B:
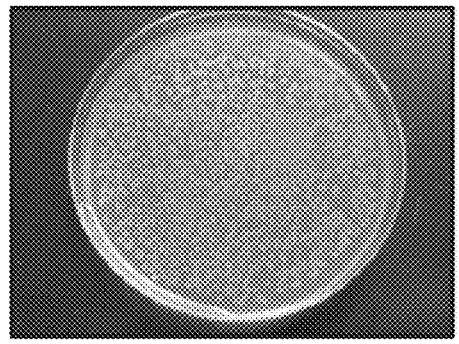
Figure 5B:
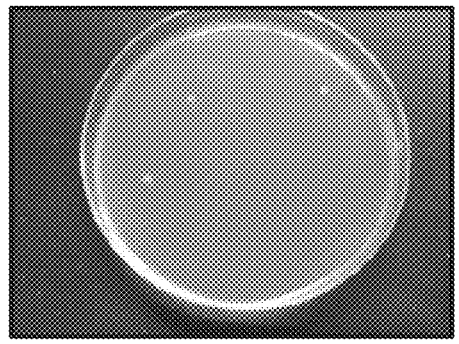
Figure 5C:
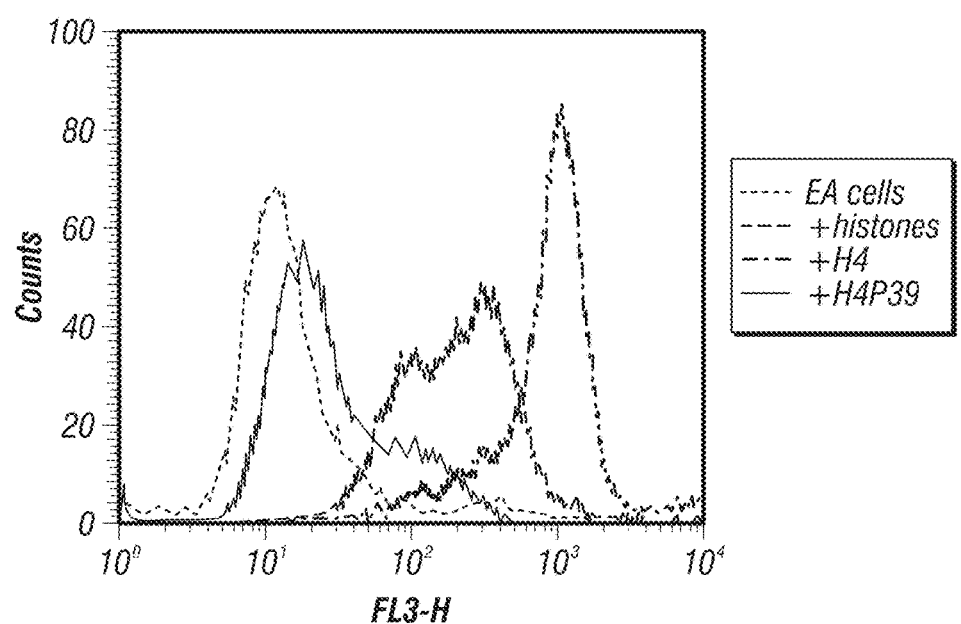
Figure 6:
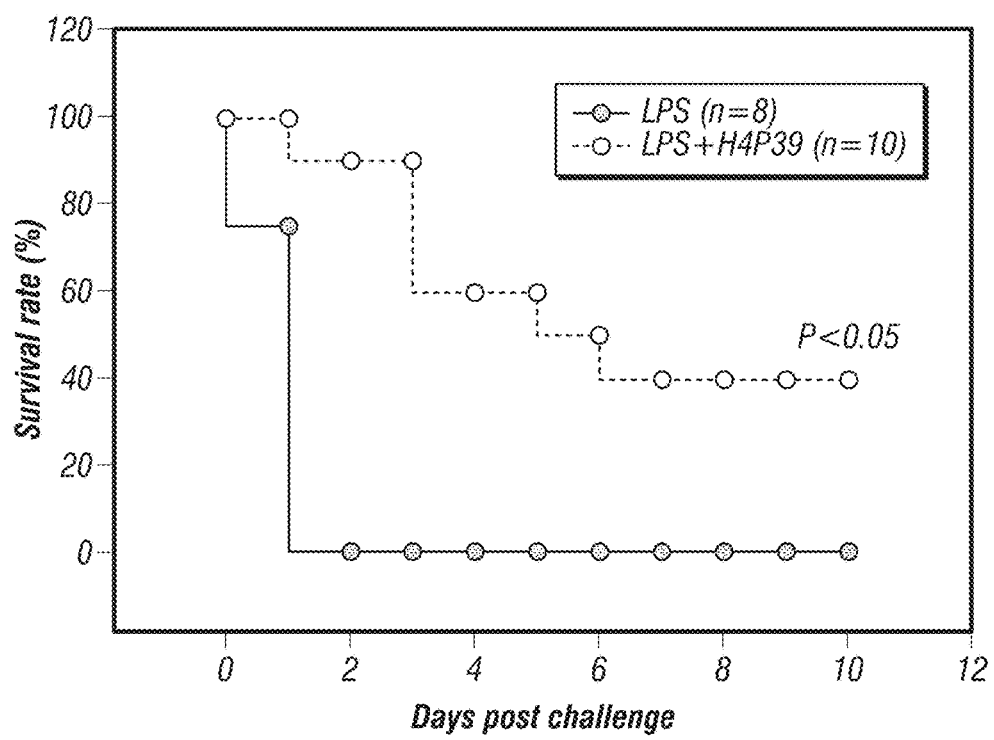
FIG. 6—H4P39 peptide rescues septic mice. Mice were intraperitoneally injected with LPS (10 mg/kg) in the absence or presence of H4P39 peptide (10 mg/kg). Survival rate of these treated mice was indicated.

Previously, a number of reports indicated that nuclear histone proteins could be detected on the surface of various cells including monocyte and neutrophil under different conditions (Herren et al., 2006; Radic et al., 2004; Emlen et al., 1992; Brinkmann et al., 2004). In this study, the inventors found that histone H4 could be released into the conditioned medium from mouse macrophages stimulated with LPS and IFN. Since extracellular histones are not only antimicrobial but also cytotoxic to mammalian cells (Hirsch, 1958; Abakushin et al., 1999; Currie et al., 1997; Kleine et al., 1997), they asked whether APC cleavage of histone could modulate these activities. The inventors treated two strains of E. coli with histones, histone H4 and one histone H4P39 peptide generated by APC (residues 40-78), and measured their bactericidal activities. FIGS. 5A-D show that H4P39 more effectively kill both strains of E. coli than histones and histone H4. In contrast, H4P39 peptide had much reduced cytotoxicity toward endothelial cells than histones and histone H4 (FIG. 5C). Co-injection of H4P39 peptide with a lethal dose of LPS significantly rescued the mice from the lethality of sepsis (FIG. 5D). These results indicate that H4P39 peptide might be a potential therapeutic in treating infectious diseases, especially for those antibiotics-resistant pathogens. This study also suggests that modulation of extracellular histone activities might be an additional mechanism for APC exerting its anti-inflammation and cytoprotection effects independent from its anti-coagulation activity and PAR-1 mediated signaling.

Upregulation of Interleukins by Histones is Blocked by APC.

Figure 7:
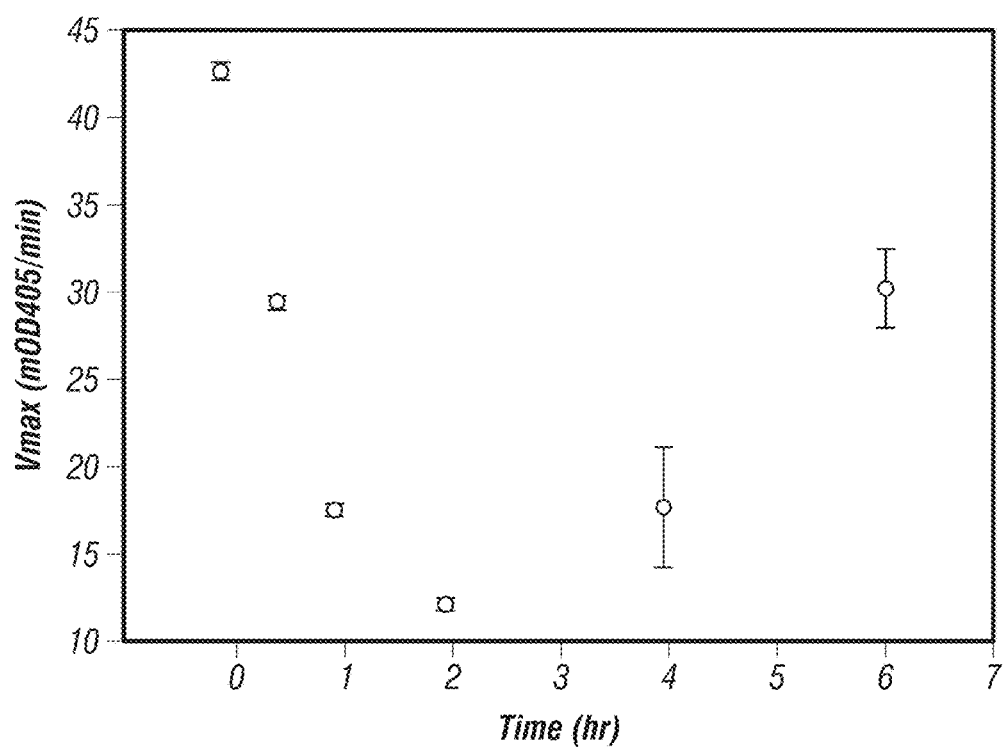
FIG. 7—Histones down-regulate the protein C activation on endothelium. EA.hy926 cells were stimulated with histones (0.1 mg/ml) for the indicated time. After wash, cells were added to 100 nM human protein C and 5 nM bovine thrombin. After 15 min at 37° C., the reaction medium was mixed with hirudin and measured for APC amidolytic activity toward PCa chromogenic substrate with $V_{max}$ reading at $OD_{405}$.
Figure 8:
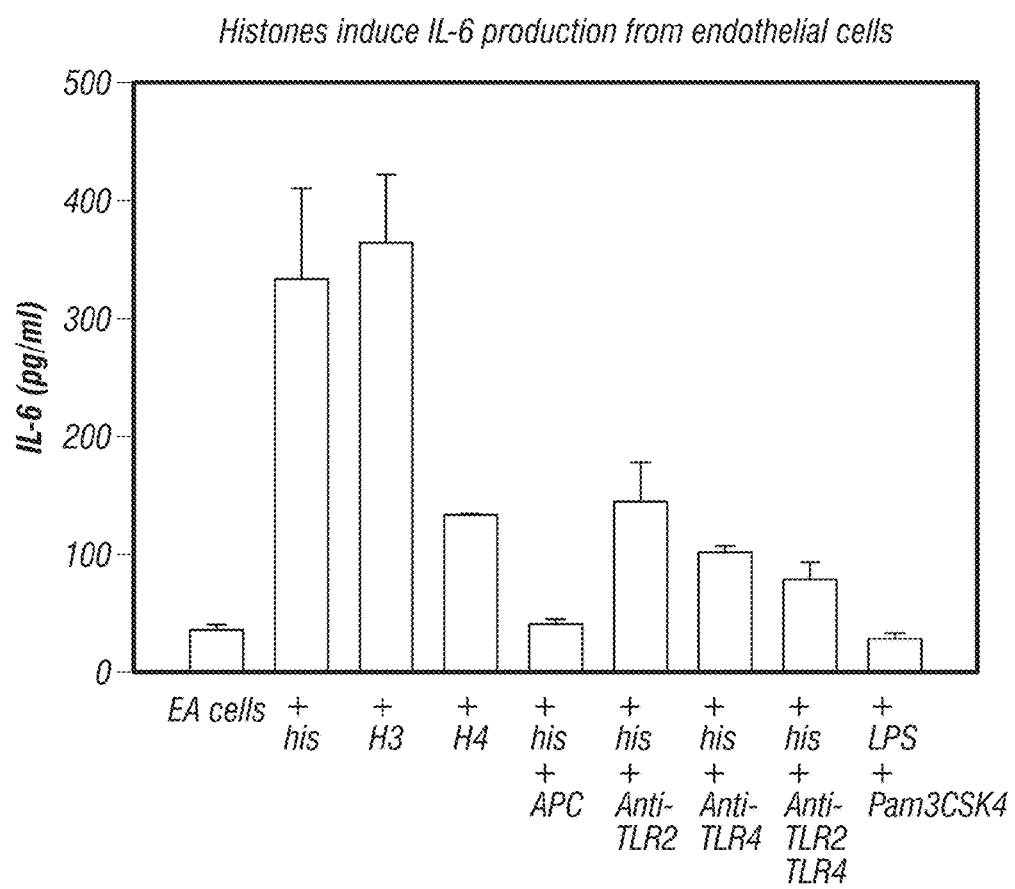
FIG. 8—Histones induce IL-6 production from endothelium. EA.hy926 cells were stimulated with histone (0.1 mg/ml) or histone H3, histone H4 (50 µg/ml) for 24 hr at 37° C. in the absence or presence of APC (6 µg/ml), Anti-TLR2, Anti-TLR4 (10 µg/ml). Conditioned medium was measured for IL-6 production by IL-6 ELISA kit.
Figure 9:
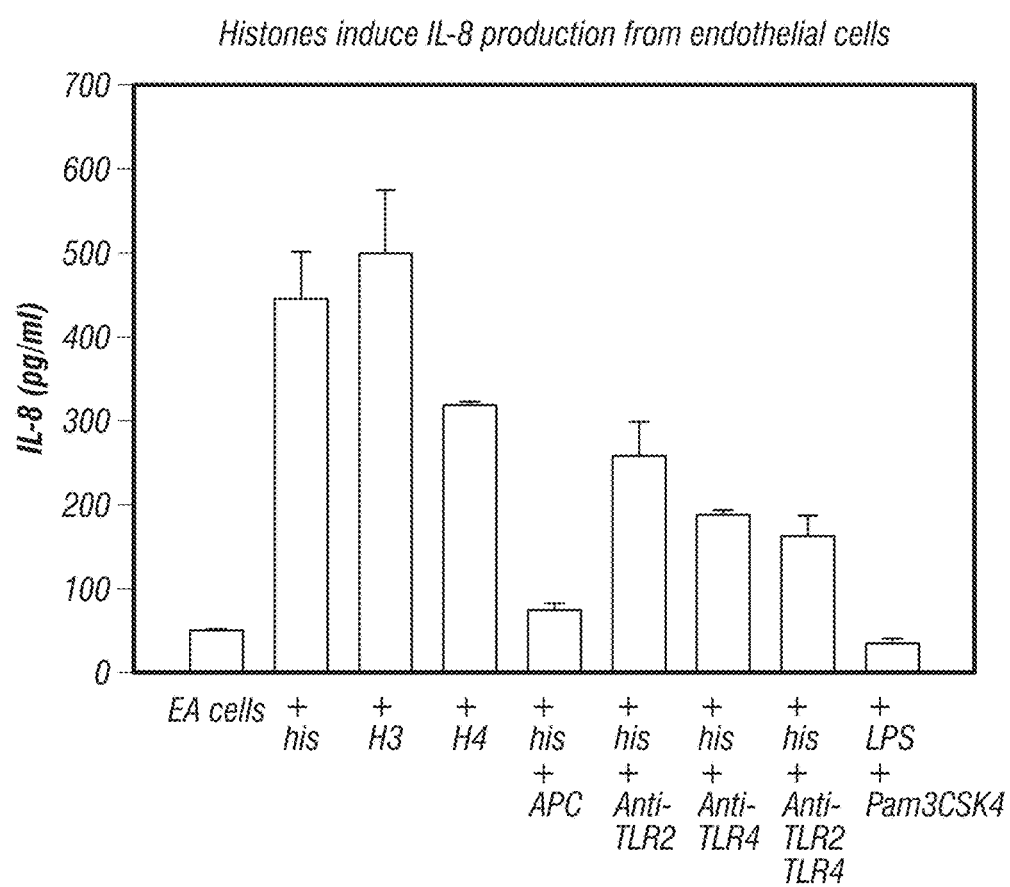
FIG. 9—Histones induce IL-8 production from endothelium. EA.hy926 cells were stimulated with histone (0.1 mg/ml) or histone H3, histone H4 (50 µg/ml) for 24 hr at 37° C. in the absence or presence of APC (6 µg/ml), Anti-TLR2, Anti-TLR4 (10 µg/ml). Conditioned medium was measured for IL-8 production by IL-6 ELISA kit.
Figure 10:
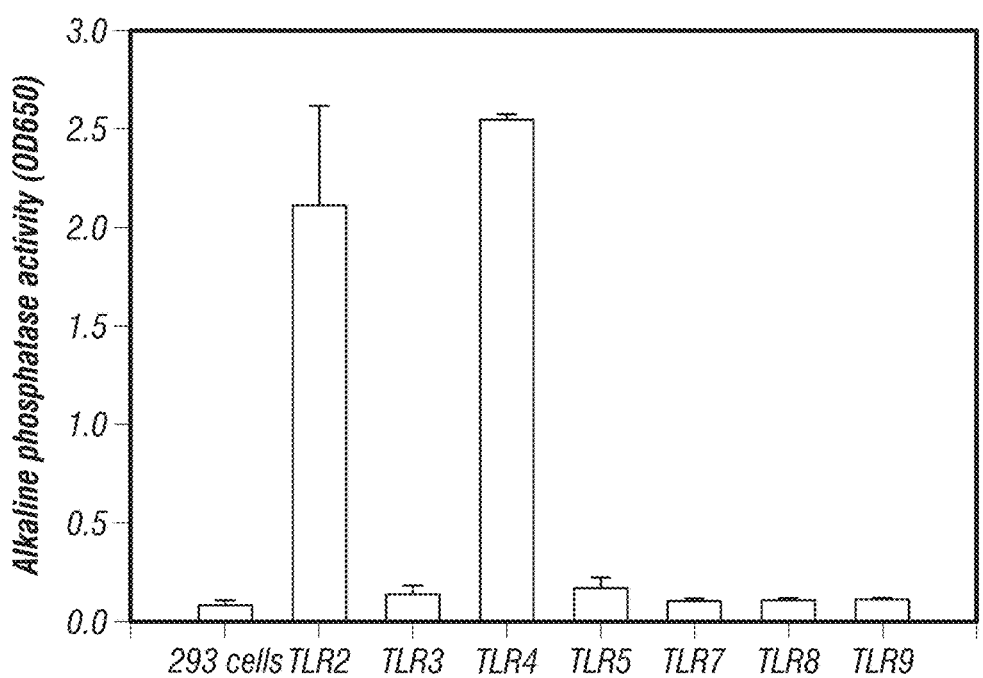
FIG. 10—Histones activate NF-κB signaling pathway via TLR-2 and TLR-4. HEK293 cells expressing an indicated human TLR with the secreted alkaline phosphatase reporter gene under the control of NF-κB signaling pathway were stimulated by histones (0.1 mg/ml) for 16 hr. Conditioned medium was measured for alkaline phosphatase activity at $OD_{650}$.

The inventors have shown that histones can decrease the anti-coagulant activity of endothelium by dramatically down-regulating proteins C activation (FIG. 7) and increasing the pro-inflammatory activity of endothelium by up-regulating IL-6 and IL-8 production (FIGS. 8-9). The up-regulation of IL-6 and IL-8 production by histones can be recaptured by histone H3 or H4, and partially inhibited by anti-TLR-2 and anti-TLR-4 antibodies, suggesting that histones may signal through TLR-2 and TLR-4. However, the exact mechanisms of histone-TLR-mediated signaling on endothelium are probably different from bacterial pathogen-TLR signaling pathways because LPS and Pam3CSK4 (a synthetic bacterial lipoprotein peptide) have no effect under this serum-free culture condition (FIGS. 8-9). Again, APC completely inhibits histone effect on IL-6 and IL-8 production (FIGS. 8-9). Human embryonic kidney 293 cells do not express TLR. TLR stimulation can be tested by assessing NF-κB activation in 293 cells expressing a given TLR. The inventors find that histones only stimulate TLR-2 and TLR-4, but not TLR-3 and TLR-5, TLR-7, TLR-8 or TLR-9 (FIG. 10). These results imply that histones may be endogenous ligands for TLR-2 and TLR-4 and play important roles in chronic cardiovascular diseases like atherosclerosis as well as tumor angiogenesis.

Figure 11:
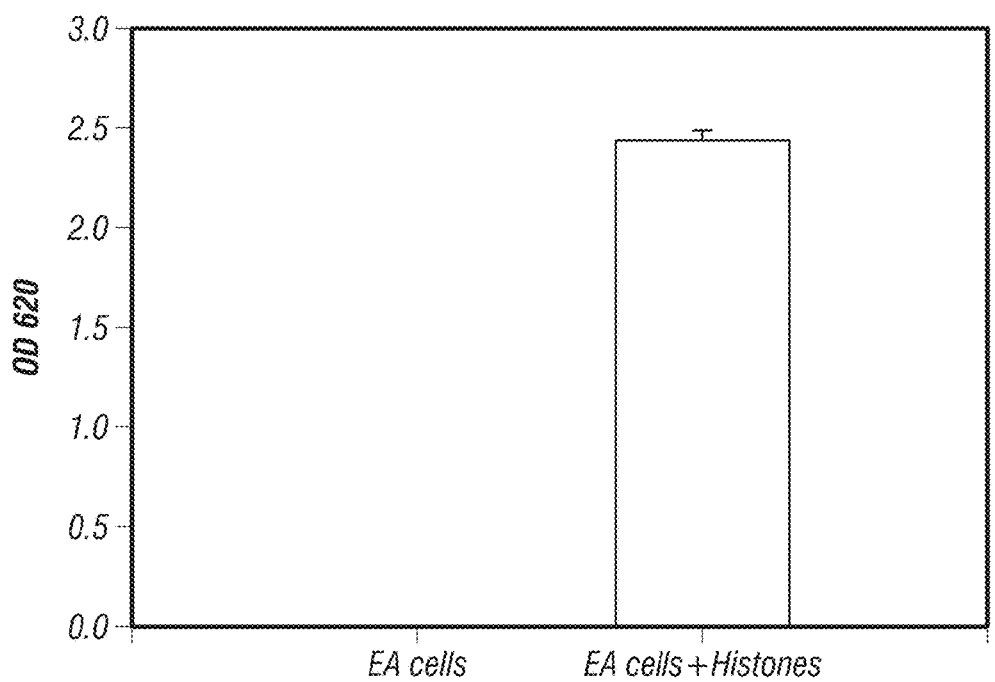
FIG. 11—Histones cause endothelial barrier dysfunction. EA.hy926 cells were incubated on the transwell for 24 hr with or without histones (0.1 mg/ml). Endothelial barrier dysfunction was measured for the leak of Evans blue-BSA from the top chamber to the bottom chamber in the transwell by $OD_{620}$.

Histones also induce endothelial permeability in vitro (FIG. 11). The molecular mechanism of this observation is under investigation. Nonetheless, the inventors believe that histone-mediated endothelial barrier dysfunction may contribute to edema, vascular leak and circulatory shock in many diseases including anthrax.

Example 3—Materials and Methods

Methods.

Human protein C, bovine thrombin and rat anti-mouse protein C mAb (MPC1609) were produced in our laboratory according to standard procedures[23]. Human recombinant APC (Xigris) was purchased from Eli Lilly. Calf thymus histones (Sigma), calf thymus histone H1, H2A, H2B, H3 and H4 (Roche), phosphatidylcholine (PC), phosphatidylserine (PS), phosphatidylethanolamine (PE) (Avanti Polar Lipids), LPS from *Salmonella typhimurium* (Sigma), murine recombinant IFN (Biosource), goat anti-histone H3 (Santa Cruz) and PPACK (Calbiochem) were also purchased. PS/PC (20:80) and PE/PS/PC (40:20:40) liposomes were prepared by membrane extrusion[11]. Mouse anti-histone H2B (LG2-2) and anti-histone H4 (BWA-3) mAbs were generated from autoimmune mice as previously described[24].

Animals.

Six to 8 week male C57BL/6 mice (Jackson Lab) were used according to an animal protocol approved by Institutional Animal Care and Use Committees of the Oklahoma Medical Research Foundation. Baboon experiments were performed as previously described[5].

Cell Culture.

The murine macrophage cell line RAW264.7 cells were cultured in RPMI 1640 medium supplemented with 10% FBS. Human endothelial cell line EA.hy926 cells were cultured in DMEM supplemented with 10% FBS and HAT (hypoxanthine, aminopterin, thymidine). Murine endothelium cell line bEnd3 cells were cultured in DMEM supplemented with 10% FBS.

Identification of Proteins from Stimulated Macrophage.

RAW264.7 cells were stimulated with 1 μg/ml LPS and 20 ng/ml IFN for 24 hr, washed with PBS, and cultured in Opti-MEM medium (Invitrogen) with or without 100 nM human APC for 24 hr. The conditioned medium was filtered through a 0.22 μm filter and concentrated 80-fold with an Amicon Ultra 10,000 (Millipore). Protein bands were electrotransferred onto PVDF membrane (Immobilon-P, Millipore) after SDS-PAGE, stained with GelCode Blue (PIERCE) and sequenced by Edman degradation (Applied Biosystems).

Histone Cytotoxicity Assay.

EA.hy926 cells were incubated with concentrated conditioned medium or various histones mixed with or without 100 nM protein C, APC or 10 nM thrombin in Opti-MEM medium at 37° C. for the indicated time and then for 5 min at room temperature after 10 μg/ml PI was added. Cells were washed and detached with 0.526 mM EDTA in PBS and subjected to flow cytometry for PI staining.

Example 4—Results

Figure 12A:
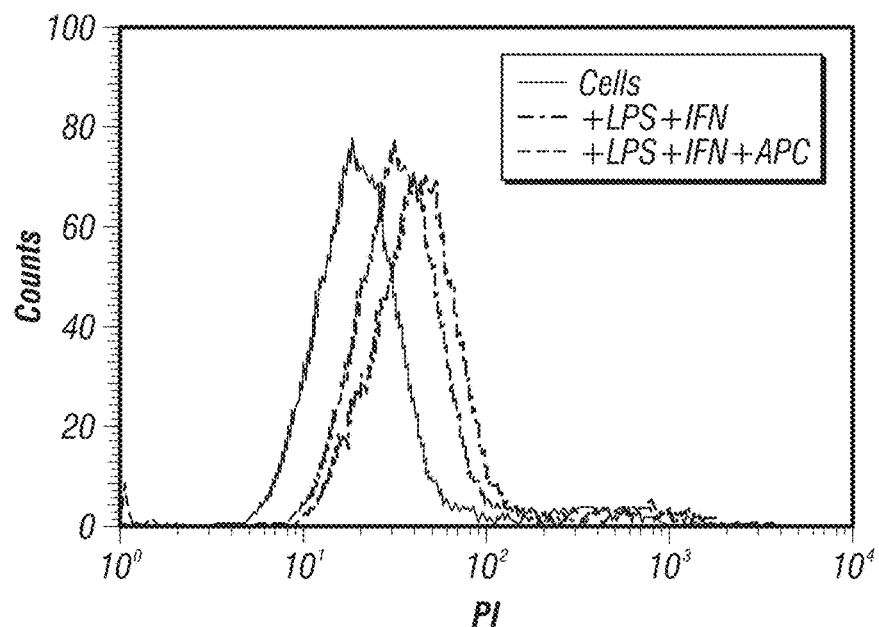
FIGS. 12A-C—Identification of extracellular histones cleaved by APC. Activated murine macrophage cells (RAW264.7) stimulated by LPS (1 µg/ml) and IFN (20 ng/ml) for 24 hr were cultured in Opti-MEM medium with or without 100 nM human APC for another 24 hr. Concentrated conditioned medium was either (FIG. 12A) measured for its cytotoxicity toward human endothelial cells (EA.hy926) after 1 hr culture by flow cytometry for PI staining or (FIG. 12B) subjected to SDS-PAGE and coomassie blue staining or (FIG. 12C) subjected to DSPAGE and Western blotting for histone H3.
Figure 12B:
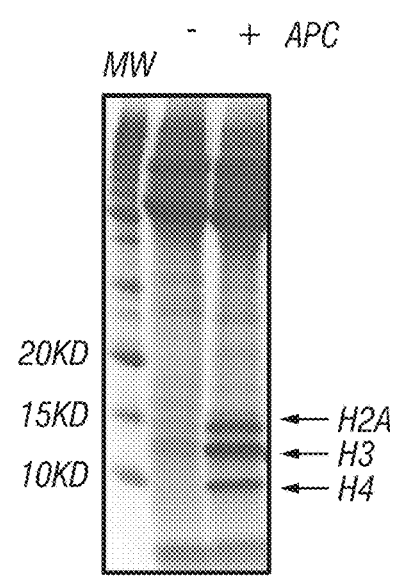
Figure 12C:
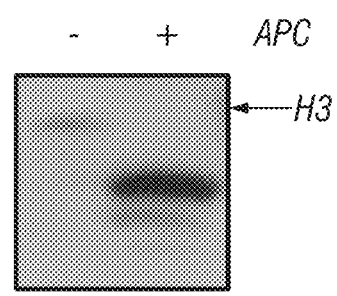

To explore potential physiological mediators involved in the pathogenesis of sepsis and molecular targets other than coagulant factors by which APC could exert its protective effect in vivo, the inventors cultured LPS and interferon gamma (IFN) activated murine macrophage RAW264.7 cells either in the presence or absence of recombinant human APC. The cytotoxicity toward endothelium was then compared between the two conditioned media. The conditioned medium from LPS and IFN activated macrophages was toxic to the human endothelial cell line, EA.hy926, as measured by propidium iodide (PI) staining APC reduced this cytotoxicity (FIG. 12A). Comparing these conditioned media by SDS-PAGE, three new major and distinct protein bands of 10 kD, 13 kD and 15 kD, appeared in the presence of APC (FIG. 12B). Edman sequencing identified XVLRDNIQGITKPAI (SEQ ID NO:14) as the N-terminal sequence of the 10 kD band protein which matches the murine histone H4 internal sequence (Val21-Ile34). The first amino acid (X) of the 10 kD protein was identified as methylated lysine (data not shown). The N-terminal sequence of the 13 kD band protein was KSAPATGGV (SEQ ID NO:15) which matches the murine histone H3 internal sequence (Lys27-Lys36). The N-terminal sequence of the 15 kD band protein could not be determined by direct Edman sequencing. Following in gel tryptic digestion, MS/MS identified three peptide sequences of AGLQFPVGR (SEQ ID NO:16), HLQLAIR (SEQ ID NO:17) and VTIAQGGVLPNIQAV-LLPK (SEQ ID NO:18) in this protein band that matches the murine histone H2A protein sequence (amino acids 21-29, 82-88 and 100-118). These data suggested that extracellular histones released from activated macrophages might be cytotoxic toward endothelium and that APC could be cytoprotective by cleaving these histones. The histone H3 identification was confirmed by Western blotting using anti-histone H3 antibody (FIG. 12D). The apparent increase in histone fragments present in the conditioned medium of activated macrophages cultured with APC might indicate that APC could not only cleave the soluble extracellular histones in the medium but also the histones associated with the activated cells.

Figure 13A:
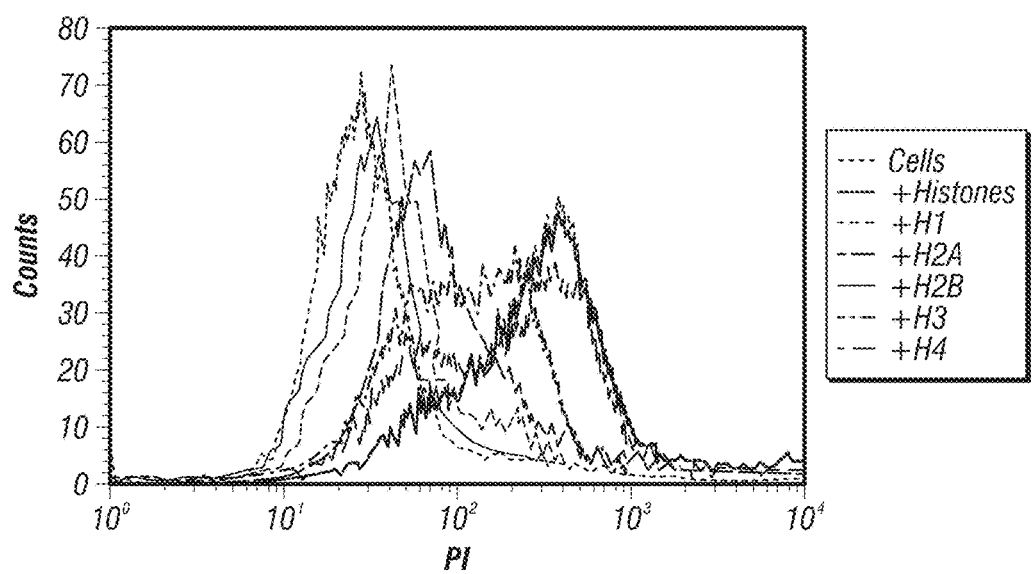
FIGS. 13A-D—Cytotoxicity of extracellular histones toward endothelium and APC cleavage of histones.
Figure 13B:
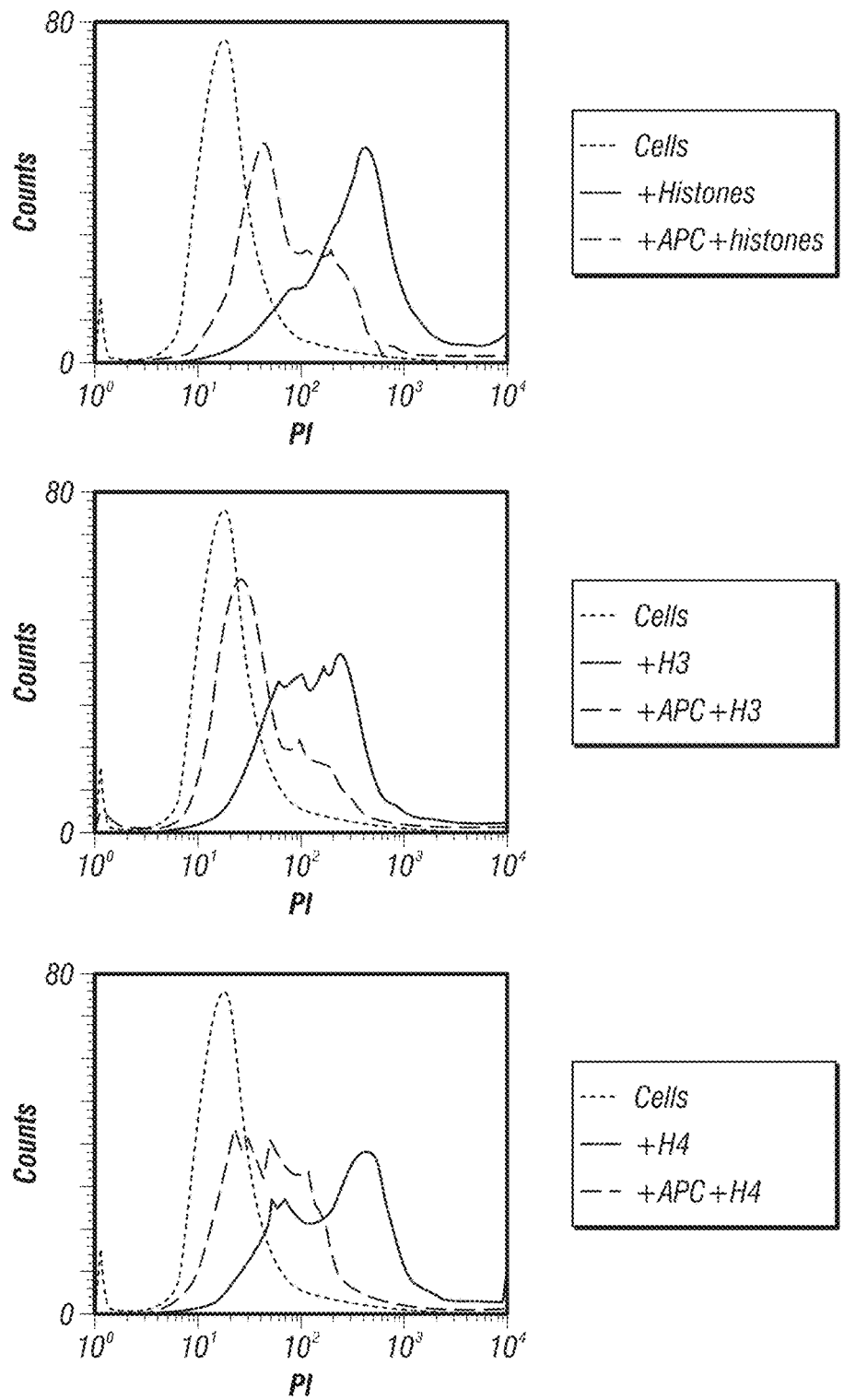
Figure 13C:
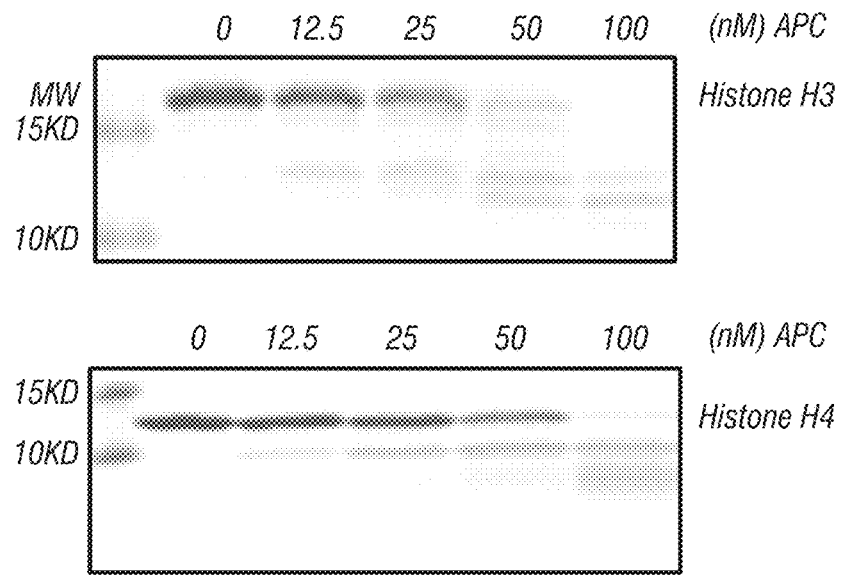
Figure 13D:
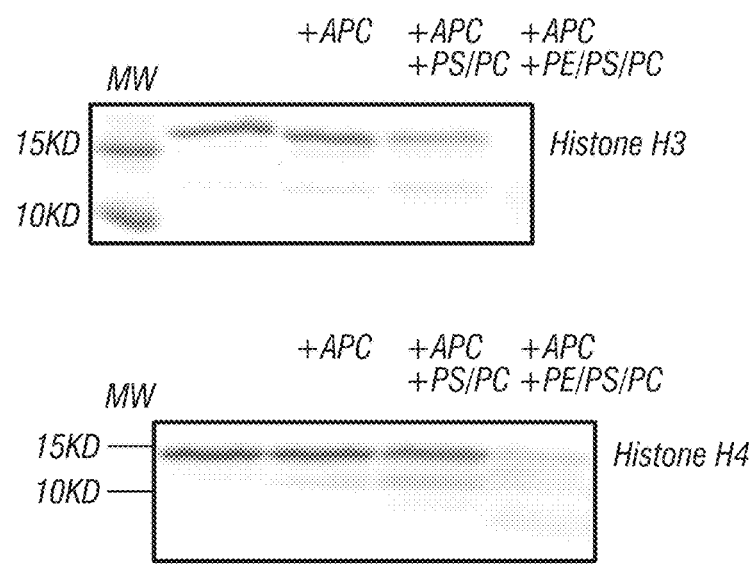

To determine if histones are toxic to endothelium and whether APC can reduce the histone cytotoxicity, the inventors treated EA.hy926 with a mixture of histones or five individual histones. FIG. 13A shows that a mixture of histones is very cytotoxic to the endothelium and this toxicity is mainly due to histone H3 and H4. Inclusion of APC dramatically reduced this cytotoxicity (FIG. 13D).

To test whether APC could cleave histones in a purified system, the inventors incubated the purified histone H3 or H4 with APC. APC cleaved histone H3 and H4 in a dose dependent fashion (FIG. 13C). Liposomes containing phosphatidylethanolamine (PE) dramatically enhanced histone cleavage by APC (FIG. 13D), similar to the effect of PE on APC inactivation of coagulation factor Va (Smirnov & Esmon, 1994). This lipid mixture is presumably a mimic of a cell surface membrane after injury or exposure to a potent agonist.

Figure 14A:
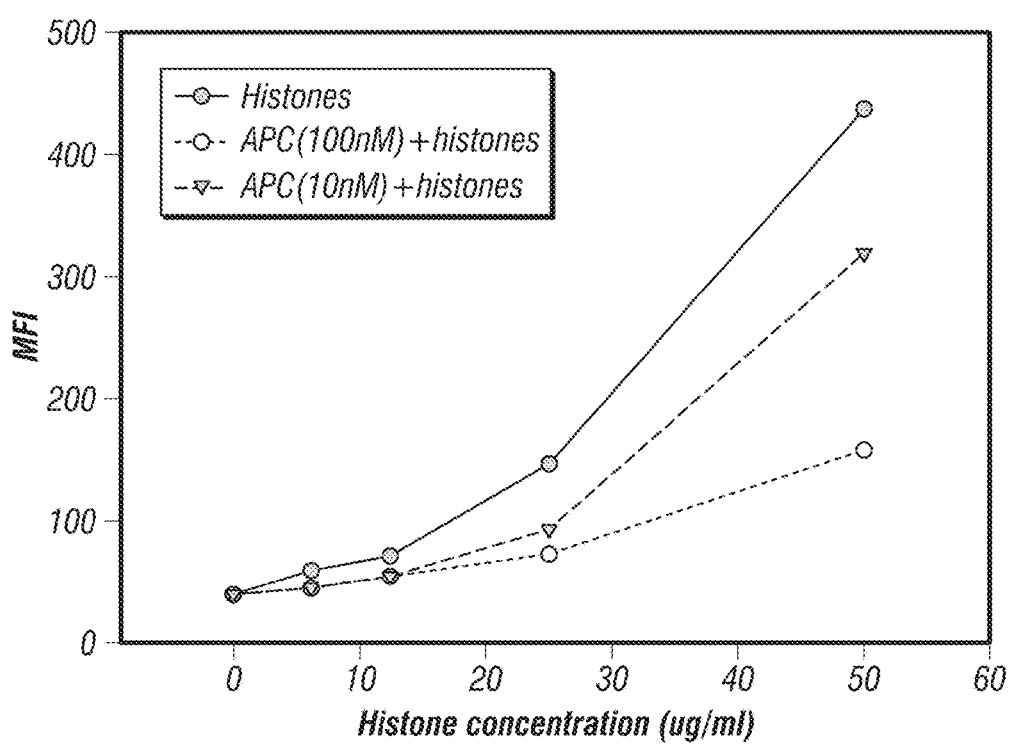
FIGS. 14A-E—APC cleaves histones both in vitro and in vivo.
Figure 14B:
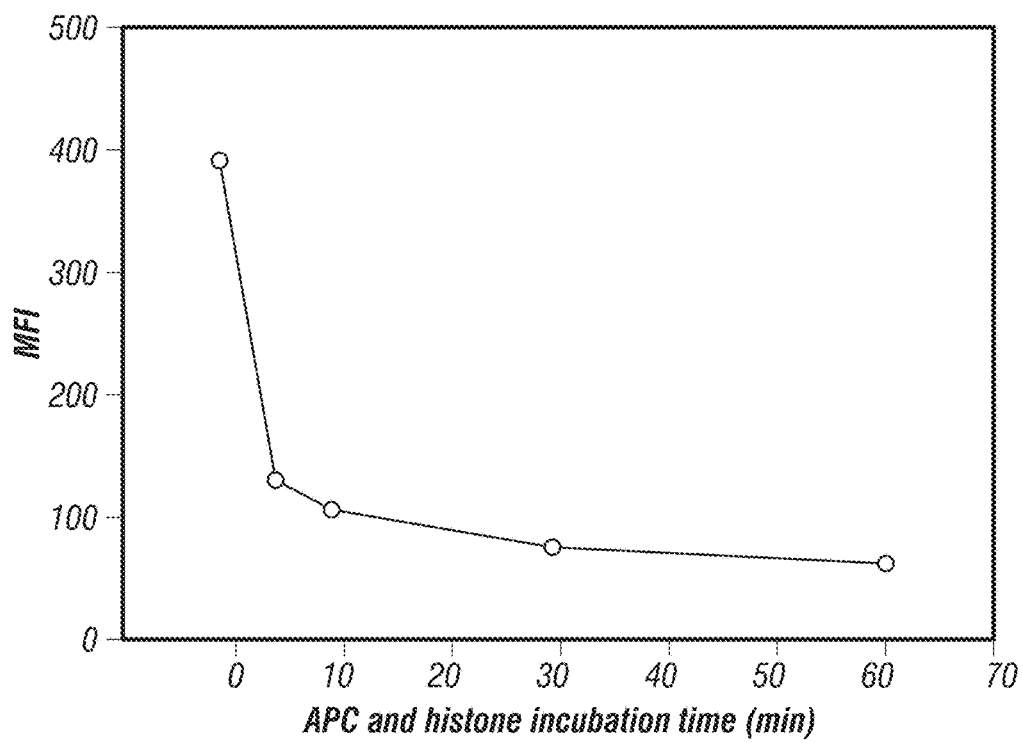
Figure 14C:
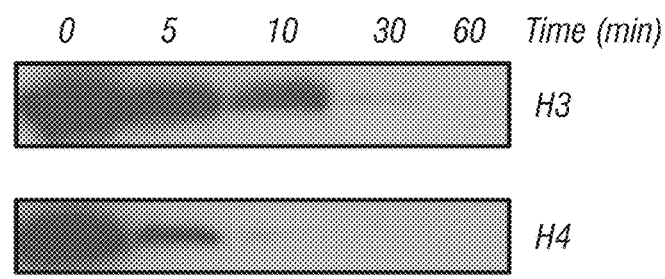
Figure 14D:
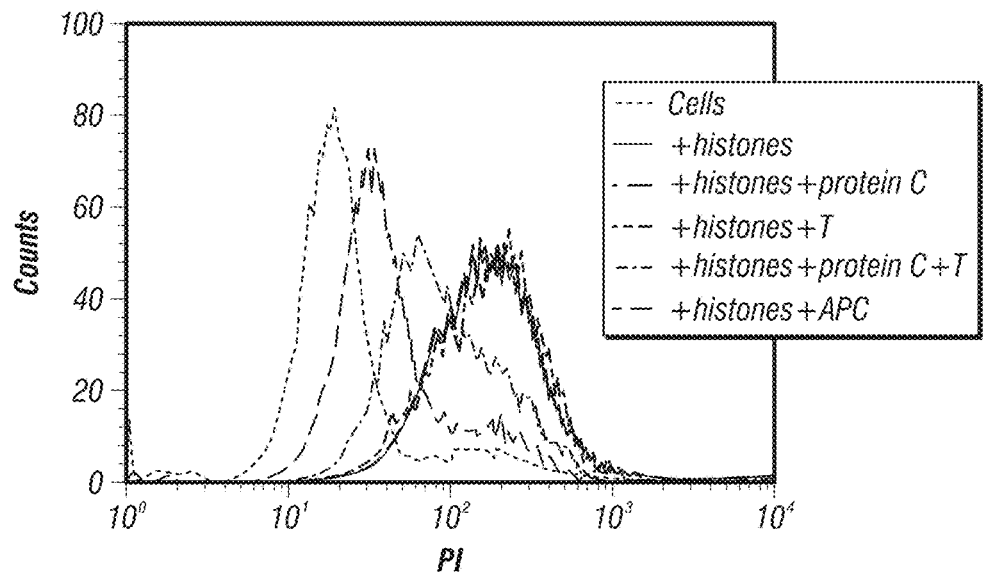

Histone cytotoxicity depends on histone concentration (FIG. 14A). 10 nM and 100 nM APC can effectively reduce the cytotoxicity of low histone concentration (25 μg/ml) but only 100 nM APC effectively reduces the cytotoxicity of histones at 50 μg/ml (FIG. 14A). Preincubation of histones (50 μg/ml) and APC (100 nM) for only 5 min eliminates most of the histone cytotoxicity (FIG. 14B). This cytoprotective effect of APC against histones is mediated by degrading histones (FIG. 14C). Cytoprotection is independent of APC mediated PAR1 signaling on endothelium because APC was inactivated by PPACK after preincubation with the histones (Riewald et al., 2002). Protein C is converted to APC by the thrombomodulinthrombincomplex on endothelium. The inventors found that the endothelial cells were not protected with either protein C or thrombin from histone cytotoxicity. The protection was only observed when both protein C and thrombin were present. Under these conditions, about 6% of the protein C was activated (FIG. 14D and data not shown). Fully activated protein C provided the best protection (FIG. 14D).

Figure 14E:
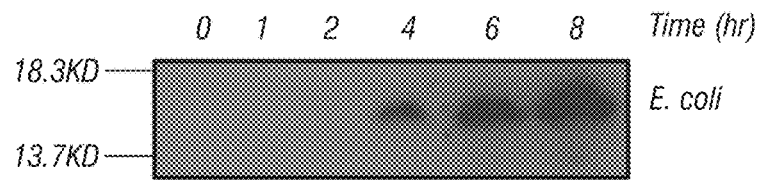
Figure 14E:

To test whether extracellular histones may be involved in the pathogenesis of diseases and if APC can cleave these histones in vivo, the inventors examined frozen archival plasma samples from a non-human primate model of sepsis in which baboons were challenged with a lethal dose of $E.$ $coli$ (Taylor et al., 1987). Infusion of APC rescued these animals (Taylor et al., 1987). The inventors measured extracellular histones in the plasma from animals challenged with the lethal dose of $E.$ $coli$ either in the absence or presence of infused APC. Intact histone H3 was detected by Western blot in the plasma of the two baboons challenged with the lethal dose of $E.$ $coli$ and reached about 15 μg/ml 8 hours post-challenge (FIG. 14E). The inventors were unable to measure other histones in the same way because those anti-histone antibodies were not adequately sensitive. The increase in histone H3 accompanied the onset of acute renal failure as indicated by a high serum creatinine level, 2.65+/−0.05 mg/dL (normal range: 0.7-1.4 mg/dL) 8 hours post-challenge. Both intact and cleaved histone H3 were observed in the plasma of two animals challenged with a lethal dose of $E.$ $coli$ and administered APC, indicating that APC can cleave extracellular histones in vivo and presumably decrease their cytotoxicity (FIG. 14E). APC co-infusion protected renal function as indicated by the normal serum creatinine level, 1.15+/−0.15 mg/dL at 8 hours post-challenge. APC cleavage of extracellular histones in the circulation, thereby protecting endothelium from histone cytotoxicity, appears to be a new mechanism contributing to its beneficial effects in sepsis.

To test the toxic effect of histones in vivo, the inventors injected 75 mg/kg of histones intravenously into mice. All mice (n=5) died within one hour after injection. Co-injection of recombinant APC (5 mg APC/kg) rescued all of the mice (n=5) challenged with the same lethal dose of histones (data not shown). The calculated histone H3 concentration in the circulation of mice injected with the lethal dose of histones is about 5 times higher than the histone H3 level detected in the baboon plasma 8 hr post challenge with $E.$ $coli$. The injected exogenous histones were rapidly cleared with a half life less than 1 minute (data not shown), indicating that the higher levels used in the infusion would fail to maintain pathologically observed levels for more than 1 min. The ratio of APC to histone H3 used to rescue the mice in vivo is similar to the ratio of APC to histone H3 used in endothelial cytoprotection experiment in vitro.

Figure 15A:
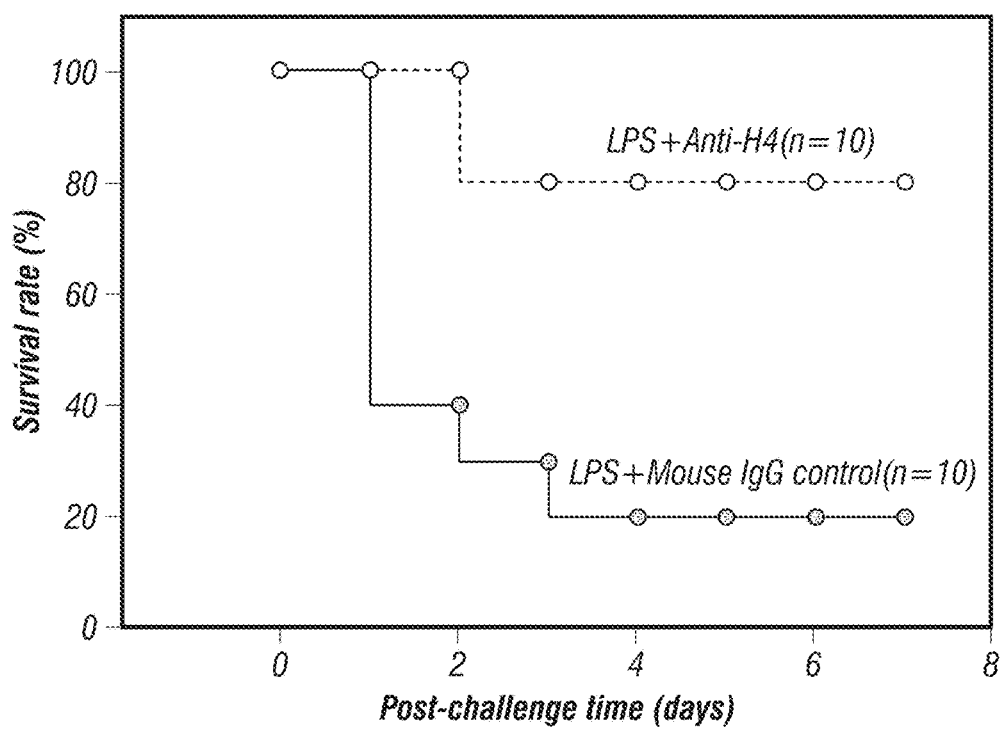
FIGS. 15A-C—Endogenous APC or anti-histone H4 mAb protects mice from the lethality of LPS in vivo.
Figure 15B:
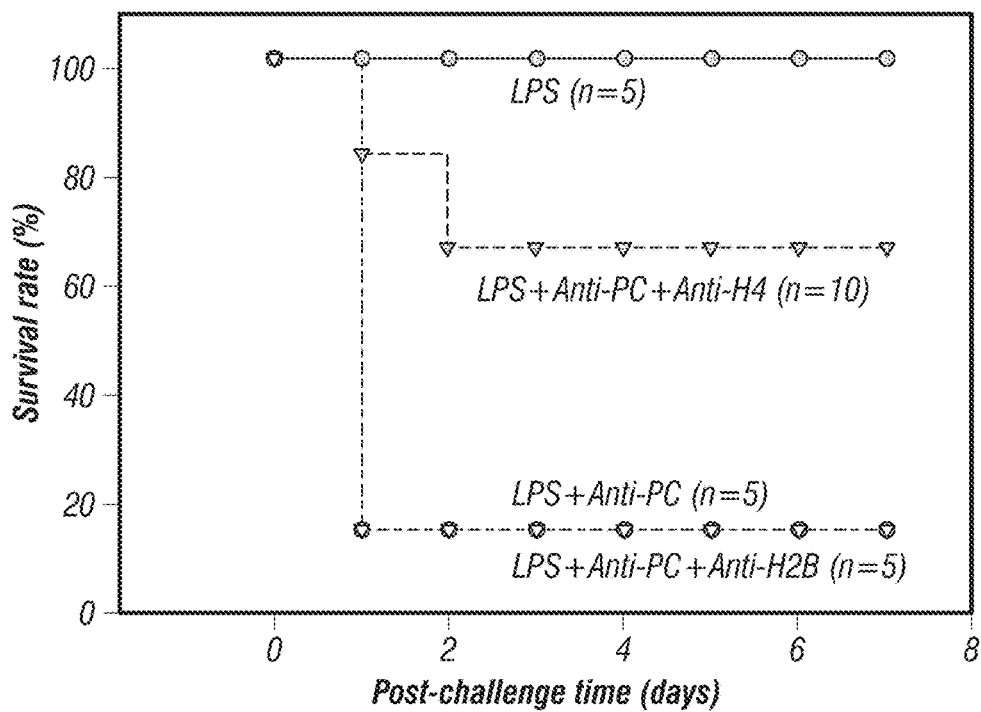
Figure 15C:
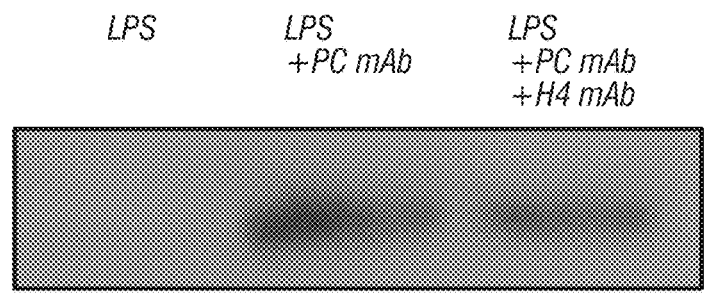

To test the pathological significance of extracellular histones in the progression of the septic response, the inventors co-infused anti-histone H4 mAb with a high dose of LPS (FIG. 15A). The anti-histone H4 mAb protected the mice from the lethal response to LPS indicating that histone H4 is a major mediator of injury in sepsis. To test whether inhibition of histone cytotoxicity by endogenous APC does indeed play a significant role in protection from death in a model of sepsis, the inventors challenged mice with a low dose of LPS in the absence or presence of an anti-mouse protein C mAb. This mAb, which blocks protein C activation both in vitro and in vivo (data not shown), converted a non-lethal into a lethal LPS dose (FIG. 15B). This result is consistent with the recent finding that acute inflammation is exacerbated in mice genetically predisposed to a severe protein C deficiency (Lay et al., 2007) and clinical observations that severe protein C deficiency is associated with early death in septic patients (Macias & Nelson, 2004). Co-infusion of anti-histone H4 mAb effectively rescued the mice from the lethality caused by LPS and the blockade of protein C activation (FIG. 15B), implying that targeting extracellular histones is an additional mechanism by which endogenous APC protects mice in this sepsis model. In contrast, the anti-histone H2B mAb failed to rescue the mice, suggesting that histone H4 is a major contributor of histone cytotoxicity in this model, consistent with the stronger cytotoxicity of histone H4 than other histones in vitro (FIG. 13A). Histone H3 was detected in plasma from mice challenged with LPS plus protein C mAb but not LPS alone (FIG. 15C), further demonstrating a critical role of APC in regulating extracellular histone levels in vivo.

Example 5—Treatment of Sepsis in Baboon Model

The treatment of sepsis by inhibition of extracellular histones was tested in a baboon model in which the baboon was pre-treated with the anti-histone H4 mAb (BWA-3). The baboon was infused with anti-histone H4 (10 mg/kg) for 30 min prior to initiation of infection. After the 30 minutes of infusion the baboon was infused with a lethal dose of $E.$ $coli$ ($2\times10^{10}$ $E.$ $coli$/kg) for 2 hours and subsequently monitored for signs of infection. Despite the lethal dose, the baboon survived for 7 days and then was sacrificed for pathology study. The pathology report indicated that except for some mild to minimal changes, the organs evaluated appeared to be essentially normal. There was no evidence of a septic disease process.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the method described herein, without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference:

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,554,101
U.S. Pat. No. 5,440,013
U.S. Pat. No. 5,446,128
U.S. Pat. No. 5,475,085
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,840,833
U.S. Pat. No. 5,859,184
U.S. Pat. No. 5,929,237
Abakushin et al., *Biochemistry (Mosc)*, 64:693-698, 1999.
Antibodies: A Laboratory Manual, Cold Spring Harbor Laboratory, Cold Spring Harbor Press, Cold Spring Harbor, N.Y., 1988.
Baltch et al., *J. Antimicrob. Chemother.*, 59(6):1177-81, 2007.
Barany and Merrifield, In: *The Peptides*, Gross and Meienhofer (Eds.), Academic Press, NY, 1-284, 1979.
Bernard et al., *NE J. Med.*, 344:699-709, 2001.
Brinkmann et al., *Science*, 303:1532-1535, 2004.
Campbell, In: *Monoclonal Antibody Technology, Laboratory Techniques in Biochemistry and Molecular Biology*, Burden and Von Knippenberg (Eds.), Elsevier, Amsterdam, 13:71-74; 75-83, 1984.
Capaldi et al., *Biochem. Biophys. Res. Comm.*, 74(2):425-433, 1977.
Clark et al., *Nat. Med.* 13, 463-469, 2007.
Currie et al., *Biochim. Biophys. Acta*, 1355:248-258, 1997.
Emlen et al., *J. Immunol.*, 148:3042-3048, 1992.
Esmon et al., *J. Autoimmun.*, 15:221-225, 2000.
Esmon, *Chest*, 124:26S-32S, 2003.
Gaini et al., *Crit. Care*, 11:R32, 2007.
Gefter et al., *Somatic Cell Genet.*, 3:231-236, 1977.
Goding, In: *Monoclonal Antibodies: Principles and Practice*, 2d ed., Academic Press, Orlando, Fla., 60-66, and 71-74, 1986.
Gupta et al., *J. Am. Soc. Nephrol.*, 18:860-867, 2007.
Herren et al., *Biochemistry*, 45:9463-9474, 2006.
Hirsch, *J. Exp. Med.*, 108:925-944, 1958.
Johannesson et al., *J. Med. Chem.*, 42(22):4524-4537, 1999.
Johnson et al., In: *Biotechnology And Pharmacy*, Pezzuto et al. (Eds.), Chapman and Hall, NY, 1993.
Kalaaji et al., *Kidney Int.*, 71:664-672, 2007.
Kleine et al., *Am. J. Physiol.*, 273:C1925-C1936, 1997.
Kohler and Milstein, *Eur. J. Immunol.*, 6(7):511-519, 1976.
Kohler and Milstein, *Nature*, 256(5517):495-497, 1975.
Kyte and Doolittle, *J. Mol. Biol.*, 157(1):105-132, 1982.
Lay et al., *Blood*, 109, 1984-1991:2007.
Macias & Nelson, *Crit. Care Med.* 32:S223-S228, 2004.
Merrifield, *Science*, 232(4748):341-347, 1986.
Monestier et al., *Mol. Immunol.*, 30:1069-1075, 1993.
Nakamura et al., In: *Handbook of Experimental Immunology* ($4^{th}$ Ed.), Weir (Eds)., 1:27, Blackwell Scientific Publ., Oxford, 1987.
Radic et al., *J. Immunol.*, 172:6692-6700, 2004.
Remington's Pharmaceutical Sciences, $15^{th}$ Ed., 1035-1038 and 1570-1580, 1990.
Riewald et al., *Science* 296, 1880-1882:2002.
Rouhiainen et al., *J. Leukoc. Biol.*, 81:49-58, 2007.
Russell, *N. Engl. J. Med.*, 355:1699-1713, 2006.
Smirnov & Esmon, *J. Biol. Chem.* 269:816-819, 1994.
Stewart and Young, In: *Solid Phase Peptide Synthesis*, 2d. ed., Pierce Chemical Co., 1984.
Tam et al., *J. Am. Chem. Soc.*, 105:6442, 1983.
Taylor et al., *J. Clin. Invest.*, 79:918-925, 1987.
Wang et al., *Science*, 285:248-251, 1999.
Weisshoff et al., *Eur. J. Biochem.*, 259(3):776-788, 1999.

What is claimed:

1. A method of inhibiting a medical condition involving extracellular histone cytotoxicity in a subject comprising administering at least a first anti-histone antibody selected from an anti-H3 antibody or an anti-H4 antibody to said subject, wherein said medical condition is severe acute pancreatitis or ischemia reperfusion injury.

2. The method of claim 1, wherein the first anti-histone antibody is an anti-H4 antibody.

3. The method of claim 1, further comprising administering to said subject a second anti-histone antibody.

4. The method of claim 3, wherein said first anti-histone antibody is an anti-H4 antibody and said second anti-histone antibody is an anti-H3 antibody.

5. The method of claim 1, wherein said subject is a human, dog, cat, horse, monkey, mouse, rat, rabbit, sheep, goat, cow or pig.

6. The method of claim 1, further comprising administering to said subject an anti-inflammatory agent.

7. The method of claim 1, further comprising administering to said subject activated protein C.

8. The method of claim 1, wherein said subject is further treated with at least one histone fragment or peptide.

9. The method of claim 1, wherein said subject is further treated with granzyme A or B, plasmin, Factor 7 activating protease, or heparin.

10. The method of claim 1, wherein said medical condition is severe acute pancreatitis.

11. A method of inhibiting severe acute pancreatitis in a subject comprising administering to a subject at least a first anti-histone antibody selected from an anti-H3 antibody and an anti-H4 antibody.

12. The method of claim 11, further comprising activated protein C.

13. A method of inhibiting pro-inflammatory cytokine production by endothelial cells in a subject with a medical condition comprising administering to said subject at least a first anti-histone antibody, wherein said first anti-histone antibody is an anti-H4 antibody, and wherein said medical condition is severe acute pancreatitis or ischemia reperfusion injury.

14. A method of reducing endothelial permeability in a subject with a medical condition comprising administering to said subject at least a first anti-histone antibody, wherein said first anti-histone antibody is an anti-H4 antibody, and wherein said medical condition is severe acute pancreatitis or ischemia reperfusion injury.

15. The method of claim 13, further comprising administering to said subject a second anti-histone antibody.

16. The method of claim 15, wherein said second anti-histone antibody is distinct from the first anti-histone antibody.

17. The method of claim 14, further comprising administering to said subject a second anti-histone antibody.

18. The method of claim 17, wherein said second anti-histone antibody is distinct from the first anti-histone antibody.

19. The method of claim 11, further comprising administering to said subject a second anti-histone antibody.

20. The method of claim 19, wherein said second anti-histone antibody is distinct from the first anti-histone antibody.

21. A method of inhibiting a medical condition involving extracellular histone cytotoxicity in a subject comprising administering to a subject a first inhibitor of cytotoxic activity, wherein the first inhibitor comprises an H4 histone peptide fragment comprises SEQ ID NO: 19, wherein said medical condition is severe acute pancreatitis or ischemia reperfusion injury.

22. A method of inhibiting pro-inflammatory cytokine production by endothelial cells in a subject comprising administering to a subject a first inhibitor of cytotoxic activity, wherein the first inhibitor comprises an H4 histone peptide fragment comprises SEQ ID NO: 19, wherein said medical condition is severe acute pancreatitis or ischemia reperfusion injury.

23. A method of reducing endothelial permeability in a subject comprising administering to a subject a first inhibitor of cytotoxic activity, wherein the first inhibitor comprises an H4 histone peptide fragment comprises SEQ ID NO: 19, wherein said medical condition is severe acute pancreatitis or ischemia reperfusion injury.

* * * * *

SEQUENCE LISTING

<160> NUMBER OF SEQ ID NOS: 19

<210> SEQ ID NO 1
<211> LENGTH: 22
<212> TYPE: DNA
<213> ORGANISM: Artificial
<220> FEATURE:
<223> OTHER INFORMATION: Synthetic primer

<400> SEQUENCE: 1
tgagagggaa atcgtgcgtg ac                22

<210> SEQ ID NO 2
<211> LENGTH: 21
<212> TYPE: DNA
<213> ORGANISM: Artificial
<220> FEATURE:
<223> OTHER INFORMATION: Synthetic primer

<400> SEQUENCE: 2

-continued gaggaagagg atgcggcagt g                                                  21

<210> SEQ ID NO 3
<211> LENGTH: 21
<212> TYPE: DNA
<213> ORGANISM: Artificial
<220> FEATURE:
<223> OTHER INFORMATION: Synthetic primer

<400> SEQUENCE: 3
cagttcgaaa gcctggtgaa g                                                  21

<210> SEQ ID NO 4
<211> LENGTH: 24
<212> TYPE: DNA
<213> ORGANISM: Artificial
<220> FEATURE:
<223> OTHER INFORMATION: Synthetic primer

<400> SEQUENCE: 4
gcagctaaca gtgagaggaa agaa                                               24

<210> SEQ ID NO 5
<211> LENGTH: 22
<212> TYPE: DNA
<213> ORGANISM: Artificial
<220> FEATURE:
<223> OTHER INFORMATION: Synthetic primer

<400> SEQUENCE: 5
gaaacttccc tggctcctat ga                                                 22

<210> SEQ ID NO 6
<211> LENGTH: 24
<212> TYPE: DNA
<213> ORGANISM: Artificial
<220> FEATURE:
<223> OTHER INFORMATION: Synthetic primer

<400> SEQUENCE: 6
agtctttgct aatctgacca gcaa                                               24

<210> SEQ ID NO 7
<211> LENGTH: 39
<212> TYPE: PRT
<213> ORGANISM: Artificial
<220> FEATURE:
<223> OTHER INFORMATION: Synthetic peptide

<400> SEQUENCE: 7

Arg Gly Gly Val Lys Arg Ile Ser Gly Leu Ile Tyr Glu Glu Thr Arg
1               5                   10                  15

Gly Val Leu Lys Val Phe Leu Glu Asn Val Ile Arg Asp Ala Val Thr
            20                  25                  30

Tyr Thr Glu His Ala Lys Arg
        35

<210> SEQ ID NO 8
<211> LENGTH: 42
<212> TYPE: PRT
<213> ORGANISM: Artificial
<220> FEATURE:
<223> OTHER INFORMATION: Synthetic peptide

<400> SEQUENCE: 8

```
Arg Leu Ala Arg Gly Gly Val Lys Arg Ile Ser Gly Leu Ile Tyr Glu
1               5                   10                  15

Glu Thr Arg Gly Val Leu Lys Val Phe Leu Glu Asn Val Ile Arg Asp
            20                  25                  30

Ala Val Thr Tyr Thr Glu His Ala Lys Arg
        35                  40
```

<210> SEQ ID NO 9
<211> LENGTH: 43
<212> TYPE: PRT
<213> ORGANISM: Artificial
<220> FEATURE:
<223> OTHER INFORMATION: Synthetic peptide

<400> SEQUENCE: 9

```
Arg Leu Ala Arg Gly Gly Val Lys Arg Ile Ser Gly Leu Ile Tyr Glu
1               5                   10                  15

Glu Thr Arg Gly Val Leu Lys Val Phe Leu Glu Asn Val Ile Arg Asp
            20                  25                  30

Ala Val Thr Tyr Thr Glu His Ala Lys Arg Lys
        35                  40
```

<210> SEQ ID NO 10
<211> LENGTH: 52
<212> TYPE: PRT
<213> ORGANISM: Artificial
<220> FEATURE:
<223> OTHER INFORMATION: Synthetic peptide

<400> SEQUENCE: 10

```
Arg Gly Gly Val Lys Arg Ile Ser Gly Leu Ile Tyr Glu Glu Thr Arg
1               5                   10                  15

Gly Val Leu Lys Val Phe Leu Glu Asn Val Ile Arg Asp Ala Val Thr
            20                  25                  30

Tyr Thr Glu His Ala Lys Arg Lys Thr Val Thr Ala Met Asp Val Val
        35                  40                  45

Tyr Ala Leu Lys
    50
```

<210> SEQ ID NO 11
<211> LENGTH: 53
<212> TYPE: PRT
<213> ORGANISM: Artificial
<220> FEATURE:
<223> OTHER INFORMATION: Synthetic peptide

<400> SEQUENCE: 11

```
Arg Gly Gly Val Lys Arg Ile Ser Gly Leu Ile Tyr Glu Glu Thr Arg
1               5                   10                  15

Gly Val Leu Lys Val Phe Leu Glu Asn Val Ile Arg Asp Ala Val Thr
            20                  25                  30

Tyr Thr Glu His Ala Lys Arg Lys Thr Val Thr Ala Met Asp Val Val
        35                  40                  45

Tyr Ala Leu Lys Arg
    50
```

<210> SEQ ID NO 12
<211> LENGTH: 56
<212> TYPE: PRT
<213> ORGANISM: Artificial
<220> FEATURE:

<223> OTHER INFORMATION: Synthetic peptide

<400> SEQUENCE: 12

Arg Gly Gly Val Lys Arg Ile Ser Gly Leu Ile Tyr Glu Glu Thr Arg
1               5                   10                  15

Gly Val Leu Lys Val Phe Leu Glu Asn Val Ile Arg Asp Ala Val Thr
            20                  25                  30

Tyr Thr Glu His Ala Lys Arg Lys Thr Val Thr Ala Met Asp Val Val
        35                  40                  45

Tyr Ala Leu Lys Arg Gln Gly Arg
    50                  55

<210> SEQ ID NO 13
<211> LENGTH: 57
<212> TYPE: PRT
<213> ORGANISM: Artificial
<220> FEATURE:
<223> OTHER INFORMATION: Synthetic peptide

<400> SEQUENCE: 13

Arg Leu Ala Arg Arg Gly Gly Val Lys Arg Ile Ser Gly Leu Ile Tyr
1               5                   10                  15

Glu Glu Thr Arg Gly Val Leu Lys Val Phe Leu Glu Asn Val Ile Arg
            20                  25                  30

Asp Ala Val Thr Tyr Thr Glu His Ala Lys Arg Lys Thr Val Thr Ala
        35                  40                  45

Met Asp Val Val Tyr Ala Leu Lys Arg
    50                  55

<210> SEQ ID NO 14
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 14

Xaa Val Leu Arg Asp Asn Ile Gln Gly Ile Thr Lys Pro Ala Ile
1               5                   10                  15

<210> SEQ ID NO 15
<211> LENGTH: 9
<212> TYPE: PRT
<213> ORGANISM: Artificial
<220> FEATURE:
<223> OTHER INFORMATION: Synthetic peptide

<400> SEQUENCE: 15

Lys Ser Ala Pro Ala Thr Gly Gly Val
1               5

<210> SEQ ID NO 16
<211> LENGTH: 9
<212> TYPE: PRT
<213> ORGANISM: Artificial
<220> FEATURE:
<223> OTHER INFORMATION: Synthetic peptide

<400> SEQUENCE: 16

Ala Gly Leu Gln Phe Pro Val Gly Arg

```
<210> SEQ ID NO 17
<211> LENGTH: 7
<212> TYPE: PRT
<213> ORGANISM: Artificial
<220> FEATURE:
<223> OTHER INFORMATION: Synthetic peptide

<400> SEQUENCE: 17

His Leu Gln Leu Ala Ile Arg
1               5

<210> SEQ ID NO 18
<211> LENGTH: 19
<212> TYPE: PRT
<213> ORGANISM: Artificial
<220> FEATURE:
<223> OTHER INFORMATION: Synthetic peptide

<400> SEQUENCE: 18

Val Thr Ile Ala Gln Gly Gly Val Leu Pro Asn Ile Gln Ala Val Leu
1               5                   10                  15

Leu Pro Lys

<210> SEQ ID NO 19
<211> LENGTH: 18
<212> TYPE: PRT
<213> ORGANISM: Artificial Sequence
<220> FEATURE:
<223> OTHER INFORMATION: Synthetic peptide

<400> SEQUENCE: 19

Ile Tyr Glu Glu Thr Arg Gly Val Leu Lys Val Phe Leu Glu Asn Val
1               5                   10                  15

Ile Arg
```